(12) United States Patent
Li et al.

(10) Patent No.: US 8,232,399 B2
(45) Date of Patent: Jul. 31, 2012

(54) CHIRAL LIGANDS, THEIR PREPARATION AND USES THEREOF IN ASYMMETRIC REACTIONS

(75) Inventors: Chao-Jun Li, Brossard (CA); Patricia MacLeod, Montreal (CA); Zhiping Li, Beijing (CN); Jianqing Feng, Suzhou (CN)

(73) Assignee: Chao-Jun Li, Brossard (CA)

( * ) Notice: Subject to any disclaimer, the term of this patent is extended or adjusted under 35 U.S.C. 154(b) by 712 days.

(21) Appl. No.: 12/281,267

(22) PCT Filed: Mar. 2, 2007

(86) PCT No.: PCT/CA2007/000348
§ 371 (c)(1),
(2), (4) Date: Jun. 19, 2009

(87) PCT Pub. No.: WO2007/098608
PCT Pub. Date: Sep. 7, 2007

(65) Prior Publication Data
US 2009/0306390 A1 Dec. 10, 2009

Related U.S. Application Data

(60) Provisional application No. 60/778,099, filed on Mar. 2, 2006.

(51) Int. Cl.
*C07D 217/02* (2006.01)
(52) U.S. Cl. ...................................... 546/149
(58) Field of Classification Search .................. None
See application file for complete search history.

(56) References Cited

PUBLICATIONS

Baran et al., "Direct coupling of pyrroles with carbonyl compounds: short enantioselective synthesis of (S)-ketorolac,"*Angew. Chem. Int. Ed.*, 44:609-612, 2005.
Bentley et al., "beta-Phenylethylamines and the isoquinoline alkaloids," *Nat. Prod. Rep.*, 21:395-424, 2004.
Bentley et al., "beta-Phenylethylamines and the isoquinoline alkaloids," *Nat. Prod. Rep.*, 22:249-268, 2005.
Bourighida et al., "Steric hindrance versus asymmetric induction: new PN-ligands for carbon-carbon coupling reactions," *Tetrahedron: Asymmetry*, 9:1073-1083, 1998.
Brown et al., "Mechanistic and synthetic studies in catalytic allylic alkylation with palladium complexes of 1-(2-diphenylphosphino-1-naphthyl)isoquinoline," *Tetrahedron.*, 50:4493-4506, 1994.
Brunel et al., "Enantioselective palladium catalyzed allylic substitution with new chiral pyridine-phosphine ligands," *Tetrahedron Lett.*, 38:5971-5974, 1997.
Cahill et al., "The application of Pd-complexes of trans-2,5-dialkylpyrrolidinyl-benzyldiphenylphosphines to enantioselective allylic alkylation," *Tetrahedron: Asymmetry*, 9:4301-4305, 1998.

Chelucci et al., "Chiral P,N-ligands with pyridine-nitrogen and phosphorus donor atoms. Syntheses and applications in asymmetric catalysis,"*Tetrahydron*, 59, 9471-9515, 2003.
Chrzanowska et al., "Asymmetric synthesis of isoquinoline alkaloids," *Chem. Rev.*, 104:3341-3370, 2004.
Dawson et al., "Asymmetric palladium catalysed allylic substitution using phosphorus containing oxazoline ligands ,"*Tetrahedron Lett.*, 34:3149-3150, 1993.
Evans et al., "Enantioselective allylic substitution using a novel (phosphino-1,3-oxazine)palladium catalyst,"*Tetrahedron Lett.*, 37:9143-9146, 1996.
Guiry et al., "The Development of Bidentate P,N Ligands for Asymmetric Catalysis," *Adv. Synth. Catal.*, 346, 49-537, 2004.
Helmchen et al., "Enantioselective palladium-catalyzed allylic substitutions with asymmetric chiral ligands," *J. Organomet. Chem.*, 576:203-214, 1999.
Hiroi et al., "(S)-Proline-derived new chiral ligands with phosphino, organosulfur or organoselenenyl functionality as an enantiocontrollable coordinating element ,"*Tetrahedron: Asymmetry*, 10:1173-1188, 1999.
Imai et al., "Diphenylphosphinooxazoline ligands with a chiral binaphthyl backbone for Pd-catalyzed allylic alkylation," *Tetrahedron Lett.*, 39:4343-4346, 1998.
Ito et al., "Asymmetric allylic alkylation using a palladium complex of chiral 2-(phosphinoaryl)pyridine ligands," *Synlett.*, 1563-1566, 1999.
Johannsen et al., "Allylic Amination," *Chem. Rev.*, 98:1689-1708, 1998.
Kubota et al., "Enantioselective palladium catalyzed allylic alkylation with phosphorus-containing $C_2$-symmetric chiral amine ligands ," *Tetrahedron Lett.*, 35(36):6689-6692, 1994.
Li et al., "Cu-catalyzed cross-dehydrogenative coupling: A versatile strategy for C-C bond formations via the oxidative activation of sp3 C-H bonds," *PNAS*, 103(24):8928-8933, 2006.
MacLeod et al., "Solvent-free direct aza-Friedel-Crafts reactions between 3,4-dihydroisoquinoline and 1- or 2-naphthols," *Tetrahedron Letters*, 47:6791-6794, 2006.

(Continued)

*Primary Examiner* — Zinna Northington Davis
(74) *Attorney, Agent, or Firm* — Fulbright & Jaworski L.L.P.

(57) ABSTRACT

A novel class of chiral ligands represented by a structure of Formula I:

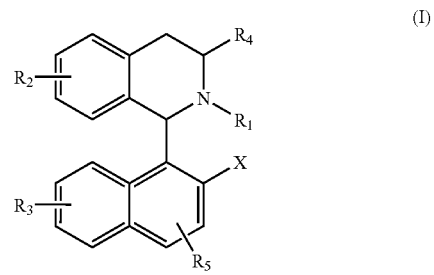

(I)

wherein $R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl; X is selected from the group consisting of OH, $OR_7$, O-Prot and $P(R_7)_2$ where Prot represents a protecting group; and $R_6$ and $R_7$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl is disclosed herein.

14 Claims, No Drawings

PUBLICATIONS

Noyori et al., "Asymmetric catalysis: Science and opportunities," *Adv. Synth. Catal.*, 345:15-32, 2003.

Ogasawara, "Synthesis and application of novel chiral phosphinooxazoline ligands with 1,1'-binaphthyl skeleton,"*Tetrahedron: Asymmetry*, 9;1779-1787, 1998.

Pelletier et al., "Synthesis of the marine alkaloids aaptamine and demethyloxyaaptamine and of the parent structure didemethoxyaaptamine," *J. Org. Chem.*, 52:616-622, 1987.

Raghunath et al., "Ferrocenyl bis-phosphine ligands bearing sulfinyl, sulfonyl or sulfenyl groups: applications in asymmetric hydrogenation and allylic alkylation reactions," *Tetrahedron Asymmetry*, 16:3676-3681, 2005.

Saitoh et al., "A Remarkable Improvement of Catalytic Performance by Electronic Substituent Effects of Chiral P-N Hybrid Ligands in Palladium-Mediated Asymmetric Allylations," *Synlett.*, 483-485, 1999.

Saitoh et al.., "A phosphorus-containing chiral amidine ligand for asymmetric reactions: enantioselective Pd-catalyzed allylic alkylation," *Tetrahedron: Asymmetry*, 8:3567-3570, 1997.

Sprinz et al., "Phosphinoaryl- and phosphinoalkyloxazolines as new chiral ligands for enantioselective catalysis: Very high enantioselectivity in palladium catalyzed allylic substitutions," *Tetrahedron Lett.*, 34:1769-1772, 1993.

Suzuki et al., "A new chiral iminophosphine ligand derived from (1$S$,4$S$)-fenchone in palladium-catalyzed asymmetric allylic alkylations," *Tetrahedron: Asymmetry*, 10:1219-1222, 1999.

Szatmari et al., "Microwave-assisted, solvent-free synthesis of 1-(α- or β-hydroxynaphthyl)-1,2,3,4-tetrahydroisoquinolines by the Mannich reaction," *Tetrahedron Letters*, 47:3881-3883, 2006.

Togni et al., "Palladium-Catalyzed Asymmetric Allylic Amination Using Ferrocenyl Pyrazole Ligands: Steric Control of $\eta^3$-Allyl Configuration and Site-Selective Nucleophilic Attack," *J. Am. Chem. Soc.*, 118:1031-1037, 1996.

Trost et al., "Asymmetric transition-metal-catalyzed allylic alkylations: applications in total synthesis," *Chem. Rev.*, 103:2921-2944, 2003.

Trost et al., "Asymmetric Transition Metal-Catalyzed Allylic Alkylations," *Chem. Rev.*, 96:395-422, 1996.

Trost et al., "On the Effect of the Nature of Ion Pairs as Nucleophiles in a Metal-Catalyzed Substitution Reaction," *J. Am. Chem. Soc.*, 120:70-79, 1998.

Venkov et al., "Synthesis of 1-Phenyl-2-acyl-tetrahydroisoquinolines by Intermolecular α-Amidoalkylation Reaction," *Synth. Commun.*, 22(1):125-134, 1992.

Von Matt et al., "Chiral Phosphinoaryldihydrooxazoles as Ligands in Asymmetric Catalysis: Pd-Catalyzed Allylic Substitution," *Chem. Int. Ed. Engl.*, 32:566-568, 1993.

Wang et al., "Synthesis of a new type of chiral amino phosphine ligands for asymmetric catalysis ," *Tetrahedron Asymmetry*, 13:1291-1297, 2002.

Wiese et al., "Chiral phosphinooxazolines with a bi- or tricyclic oxazoline moiety—applications in Pd-catalyzed allylic alkylations," *Tetrahedron Lett.*, 39:5727-5730, 1998.

Wimmer et al., "New chiral aminophosphines and their use in asymmetric catalysis," *Tetrahedron: Asymmetry*, 6:657-660, 1995.

Yonehara et al., "Palladium-catalysed asymmetric allylic alkylation using new chiral phosphinite—nitrogen ligands derived from D-glucosamine,"*Chem. Commun.*, 415-416, 1999.

Zhang et al., "Novel chiral P,N-ferrocene ligands in palladium-catalyzed asymmetric allylic alkylations," *Tetrahedron: Asymmetry*, 9:3371-3380, 1998.

CHIRAL LIGANDS, THEIR PREPARATION AND USES THEREOF IN ASYMMETRIC REACTIONS

CROSS REFERENCE TO RELATED APPLICATIONS

This application is a national phase application under 35 U.S.C. §371 of International Patent Application PCT Application No. PCT/CA2007/000348, filed 2 Mar. 2007, which claims the benefit of U.S. Provisional Application 60/778,099 filed 2 Mar. 2006. The entire contents of these applications are incorporated by reference.

FIELD OF THE INVENTION

The present disclosure broadly relates to chiral ligands, their preparation and uses thereof in asymmetric reactions. More specifically, but not exclusively, the present disclosure relates to chiral N, O and N, P ligands, their preparation and use in asymmetric catalysis.

BACKGROUND OF THE INVENTION

The discovery of novel enantioselective reactions to generate optically active compounds plays a fundamental role in pharmaceutical research and represents one of the most important developments in modern organic chemistry.[1] Many organic compounds of interest as pharmaceuticals and pesticides are chiral and very often only one of the enantiomers is effective or desirable for biological purposes. With the growing demand for enantiomerically pure compounds, asymmetric catalysis has become increasingly more important because of its high efficiency.

Asymmetric catalysis takes advantage of chiral catalysts to generate chiral compounds. The area of transition metal-catalyzed asymmetric reactions has witnessed the development of numerous novel chiral ligands.[2] Among the many chiral catalysts developed, the chiral ligands BINAP, QUINAP and BINOL have proven to be particularly effective in catalyzing asymmetric reactions (Scheme 1). A general feature of these ligands comprises the presence of a single chiral axis. Chiral N, P ligands comprise an important type of chirality transfer agent for asymmetric catalysis.[3]

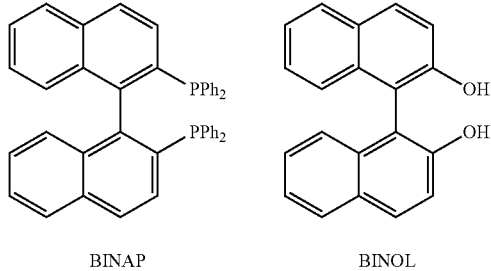

BINAP  BINOL

Scheme 1

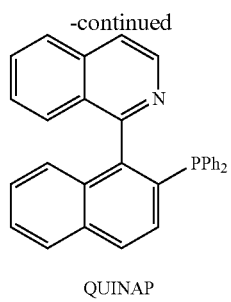

QUINAP

Palladium-catalyzed asymmetric allylic substitution reactions, by means of chiral ligands, remain of continued interest in the synthetic community large because of their synthetic potential.[4] Recently, non-symmetric heterobidentate ligands have been found to be efficient chiral sources for asymmetric allylic substitution reactions. These ligands regulate the enantioselectivity through their steric and ligand effects. In particular, the coordination of ligand atoms of different rows of the periodic table affects the susceptibility of the π-allyl terminal to nucleophiles in a different way (trans-effect), resulting in a highly regioselective nucleophilic attack.[5] Some successful examples of such bidentate ligands comprise the 2-(phosphinoaryl)oxazoline ligands[4a-c] (Scheme 2) and the (phosphinonaphthyl) isoquinoline (QUINAP) ligand.[4d]

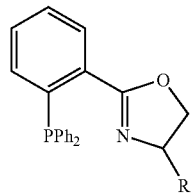

Scheme 2

While these ligands have been useful in a number of asymmetric reactions, there are still many more asymmetric transformations that can benefit from the discovery of new chiral ligands.

The present disclosure refers to a number of documents, the contents of which are herein incorporated by reference in their entirety.

Objects of the Invention

The present disclosure relates to chiral N, O and N, P ligands.

In an embodiment, the present disclosure relates to chiral ligands represented by a structure of Formula I:

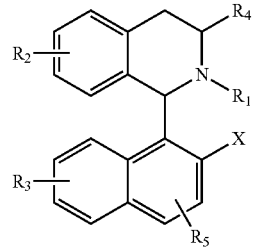

Formula I wherein:

$R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl;

X is selected from the group consisting of OH, $OR_7$, O-Prot and $P(R_7)_2$; and $R_6$ and $R_7$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl.

In an embodiment, the present disclosure relates to chiral ligands selected from the group consisting of:

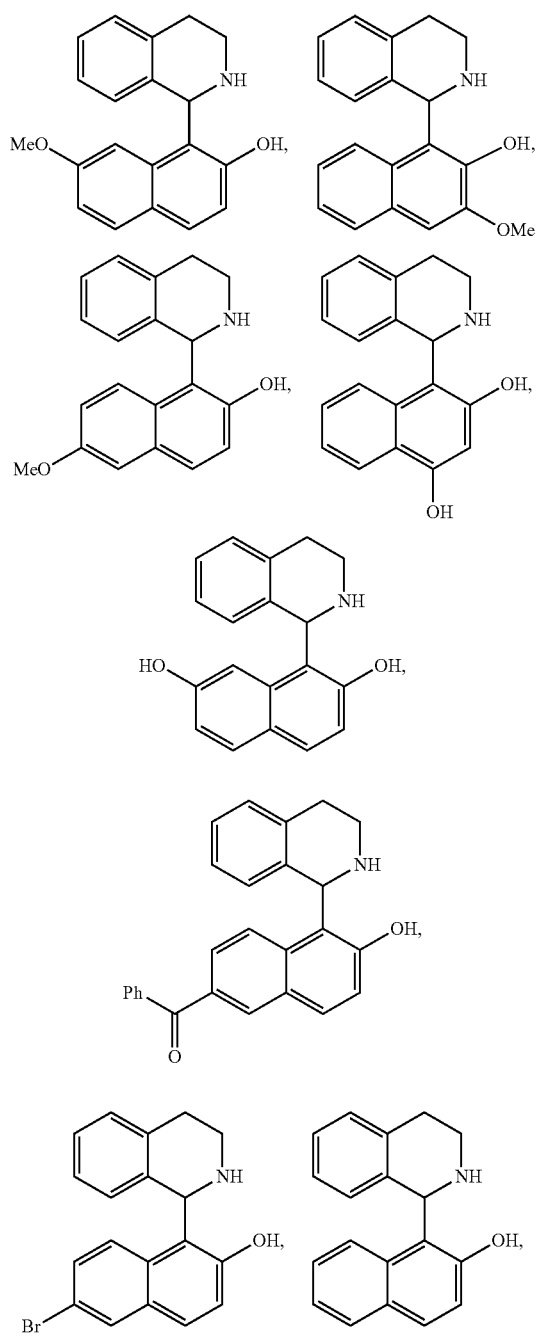

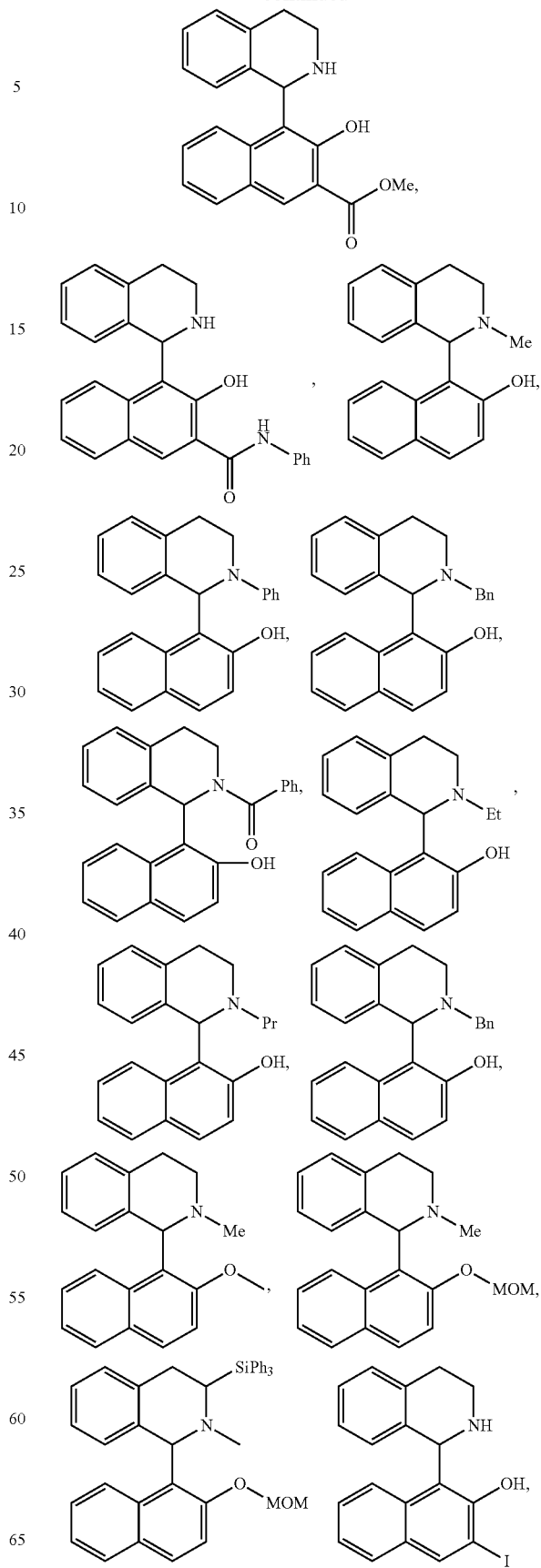

-continued

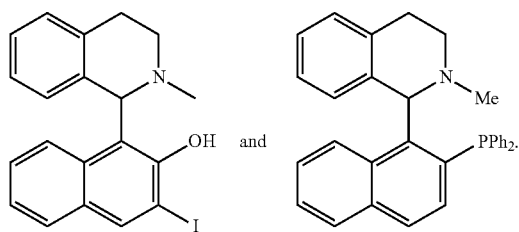

In an embodiment, the present disclosure relates to a racemic mixture of chiral ligands of Formula I.

In an embodiment, the present disclosure relates to a non-racemic mixture of chiral ligands of Formula I.

In an embodiment, the present disclosure relates to chiral ligands of Formula I, selected from the group consisting of L and R enantiomers.

In an embodiment, the present disclosure relates to chiral ligands of Formula I, comprising the L-enantiomer.

In an embodiment, the present disclosure relates to chiral ligands of Formula I, comprising the R-enantiomer.

In an embodiment, the present disclosure relates to a process for preparing chiral ligands represented by a structure of Formula I:

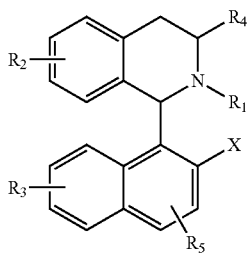

Formula I wherein:

$R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl;

X is selected from the group consisting of OH, $OR_7$, O-Prot and $P(R_7)_2$; and $R_6$ and $R_7$ are selected from the group consisting of hydrogen, $C_{1-10}$ alkyl, $C_{2-10}$ alkenyl, $C_{3-10}$ alkenyl, $C_{1-10}$ alkoxy, phenyl, and aryl; comprising reacting a compound of Formula Ia:

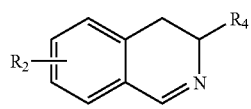

Formula Ia with a compound of Formula Ib

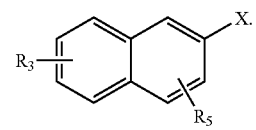

Formula Ib

In an embodiment, the present disclosure relates to a use of the chiral ligands represented by a structure of Formula I:

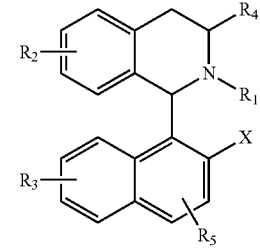

Formula I wherein:

$R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl;

X is selected from the group consisting of OH, $OR_7$, O-Prot and $P(R_7)_2$; and $R_6$ and $R_7$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl;

in asymmetric reactions.

Further scope and applicability will become apparent from the detailed description given hereinafter. It should be understood however that this detailed description, while indicating preferred embodiments, is given by way of example only, since various changes and modifications will become apparent to those skilled in the art.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "carbonyl" as used herein, represents a C(O) group, which can also be represented as C=O.

The terms "carboxy" or "carboxyl," as used interchangeably herein, represents a $CO_2H$ group.

The term "halogen" as used herein is understood as referring to fluorine, chlorine, bromine, or iodine. Correspondingly, the meaning of the term "halo" is understood to encompass fluoro, chloro, bromo, and iodo.

The term "hydroxy" or "hydroxyl," as used interchangeably herein, represents an —OH group.

The term "alkyl group" as used herein is understood as referring to a saturated, monovalent unbranched or branched hydrocarbon chain. Examples of alkyl groups include, but are not limited to, $C_{1-10}$ alkyl groups. Examples of $C_{1-10}$ alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl.

The term "alkenyl" as used herein is understood as referring to monovalent straight or branched chain groups of, unless otherwise specified, from 2 to 10 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like.

The term "alkynyl" as used herein is understood as referring to monovalent straight or branched chain groups of from 2 to 10 carbon atoms comprising one or more carbon-carbon triple bonds and is exemplified by ethynyl, 1-propynyl, and the like.

The terms "alkoxy" or "alkyloxy," as used interchangeably herein, represent an alkyl group attached to the parent molecular group through an oxygen atom. Exemplary unsubstituted alkoxy groups comprise from 1 to 10 carbons.

The term "aryl" as used herein is understood as referring to 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions. Aryl groups can also be part of a polycyclic group. For example, aryl groups include fused aromatic moieties such as naphthyl, anthracenyl, quinolyl, indolyl, and the like.

The term "protecting group" or "prot" as used in the present specification has the meaning usual in synthetic chemistry, particularly for hydroxyl group protection. It refers to any group that may be covalently bound to a hydroxy group, protecting it from undesirable reactions during synthetic procedures. Commonly used hydroxyl-protecting groups are disclosed in Greene, "Protective Groups In Organic Synthesis, 3$^{rd}$ Edition" (John Wiley & Sons, New York, 1999), which is incorporated herein by reference. Non-limiting suitable protecting groups include t-butyl ethers, benzyl ethers, silyl ethers, MOM (methoxy methyl ethers), MEM (2-methoxy ethoxy methyl ethers) and acetates.

The present specification refers to a number of chemical terms and abbreviations used by those skilled in the art. Nevertheless, definitions of selected terms are provided for clarity and consistency.

Abbreviations: NMR: Nuclear Magnetic Resonance; MS: Mass Spectrometry; m.p.: melting point; HRMS: High Resolution Mass Spectrometry; EtOAc: Ethyl acetate; $CH_2Cl_2$: Dichloromethane; $CDCl_3$: Chloroform-d; DBU: 1,8-diazabicyclo[5.4.0]undec-7-ene; THF: Tetrahydrofuran; TFA: Trifluoroacetic acid; TBDPS: t-Butyldiphenylsilyl; AcOH: Acetic acid; TLC: Thin Layer Chromatography; FAB: Fast Atom Bombardment.

Tetrahydroisoquinoline derivatives widely exist in nature and exhibit a wide range of biological and pharmaceutical properties.[6,7] In an embodiment, the present disclosure relates to chiral ligands represented by a structure of Formula I:

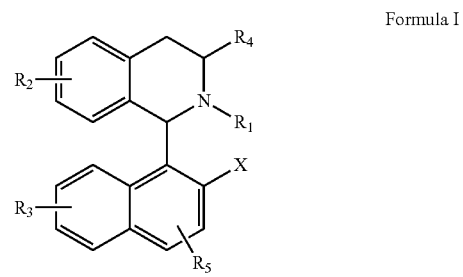

Formula I wherein:

$R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl;

X is selected from the group consisting of OH, $OR_7$, O-Prot and $P(R_7)_2$; and $R_6$ and $R_7$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl.

Non-limiting examples of such chiral ligands are illustrated hereinbelow in Scheme 1. 1-Naphthol and derivatives thereof can also be used for the preparation of chiral ligands as contemplated by the present disclosure. Yet further naphthol derivatives are known in the art and are within the capacity of a skilled technician.

Scheme 1

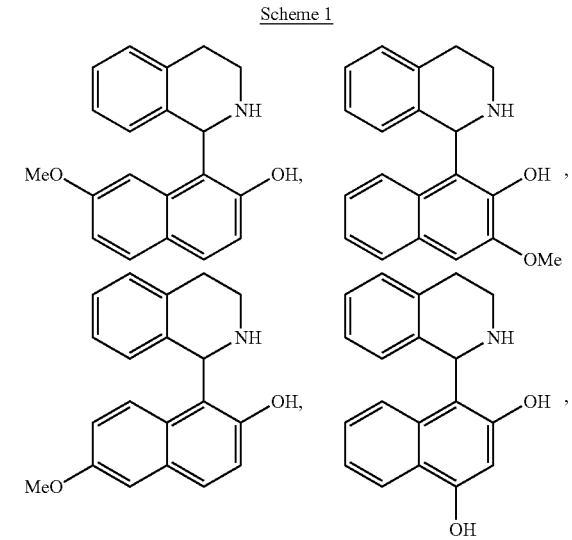

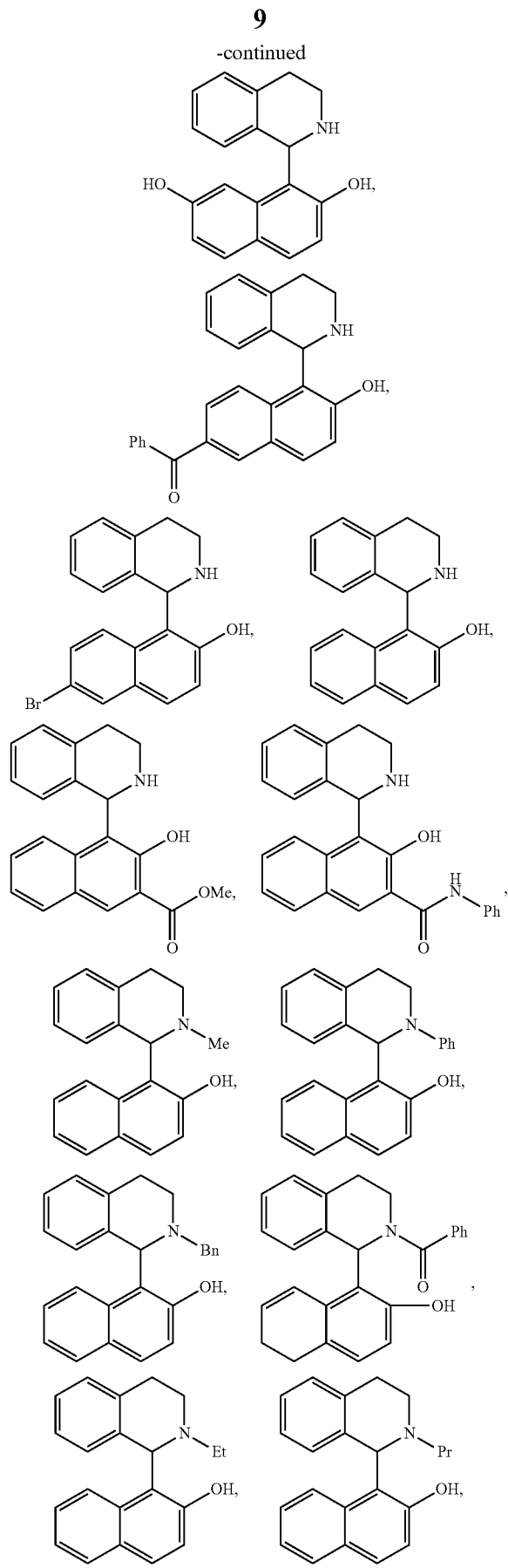
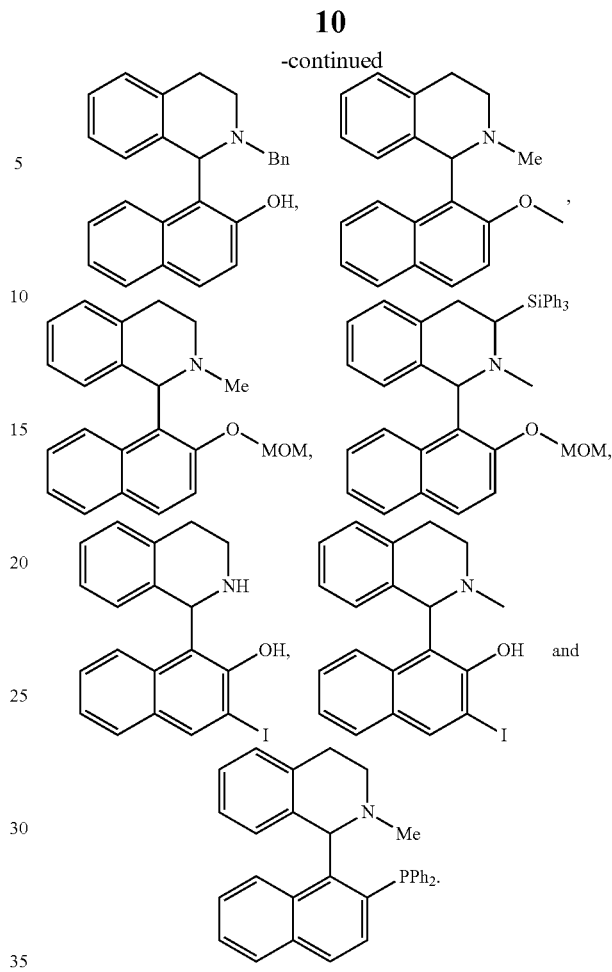

The chiral ligands of the present disclosure can be substituted or modified by yet other substituents. Such other substituents are known in the art, and are within the capacity of a skilled technician. In a non-limiting embodiment, $R_2$, $R_3$, $R_4$ and $R_5$ can be selected from the group consisting of —$CO_2H$, —$CO_2M$ (M is selected from the group of metal ions, ammonium ions and phosphonium ions), —$CO_2R$, —$SO_3H$, —$SO_3M$ (M is selected from the group of metal ions, ammonium ions and phosphonium ions), —$SO_2R$, —$PO_3H_2$, —$PO_3M_2$ (M is selected from the group of metal ions, ammonium ions and phosphonium ions), —CN, —$NO_2$, —SH, —SR(R=$C_{1-10}$ alkyl), —SM (M is selected from the group of metal ions, ammonium ions and phosphonium ions), —$NH_2$, —NHR, —N(R)$_2$, —NHCOR, —NHC(=)O—NHR, —NHC(=)S—NHR, —$RSO_3H$, —$RSO_3M$ (M is selected from the group of metal ions, ammonium ions and phosphonium ions), —$RCO_2H$, —$RCO_2M$ (M is selected from the group of metal ions, ammonium ions and phosphonium ions), —R—OH, -aryl-$SO_3H$ and -aryl-$SO_3M$ (M is selected from the group of metal ions, ammonium ions and phosphonium ions); wherein R is an alkyl group.

In an embodiment, the chiral ligands of the present disclosure can be used in the asymmetric synthesis of biological compounds having therapeutic and/or prophylactic properties. In a further embodiment, the chiral ligands of the present disclosure can be used in asymmetric catalysis processes leading to the asymmetric synthesis of biological compounds having therapeutic and/or prophylactic properties.

In an embodiment, the chiral ligands of the present disclosure can be supported onto a chiral auxiliary, polymer, silica gel, ionic liquids, and perfluoroalkyls for supported synthesis, combinatorial synthesis, and for catalyst/product recovery (Scheme 2).

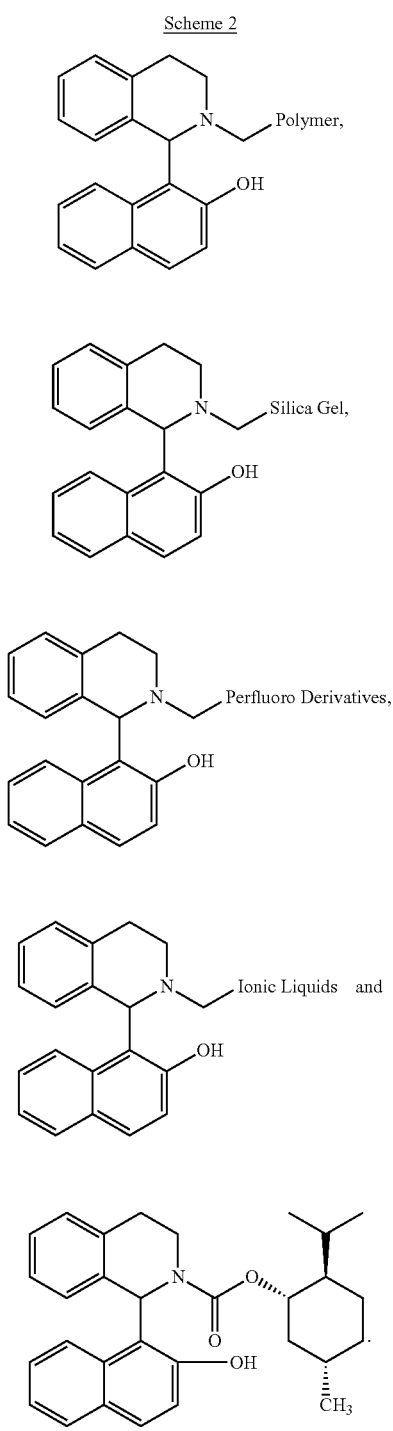

In an embodiment of the present disclosure, 3,4-dihydroisoquinoline was reacted with 1-naphthol yielding the desired product in 92% yield as a single regio-isomer (Scheme 3).

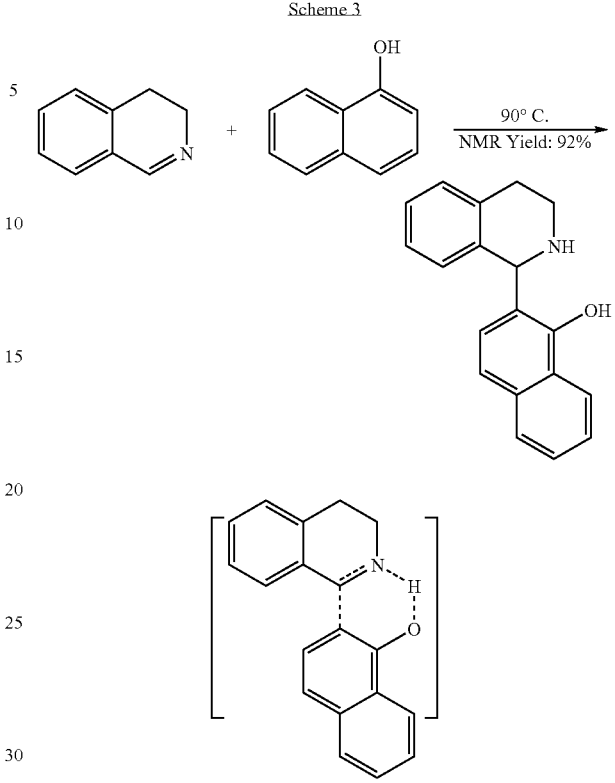

In a further embodiment of the present disclosure, 3,4-dihydroisoquinoline was reacted with 2-naphthol under neat conditions, yielding the desired product in high yield (Scheme 4). The reaction can also be carried out in non-anhydrous conditions (i.e. air) without any substantial reduction in the product yield. Interestingly, the use of solvents such as toluene, THF and dichloroethane resulted in lower product yields (i.e. 41%, 6% and 20% respectively).

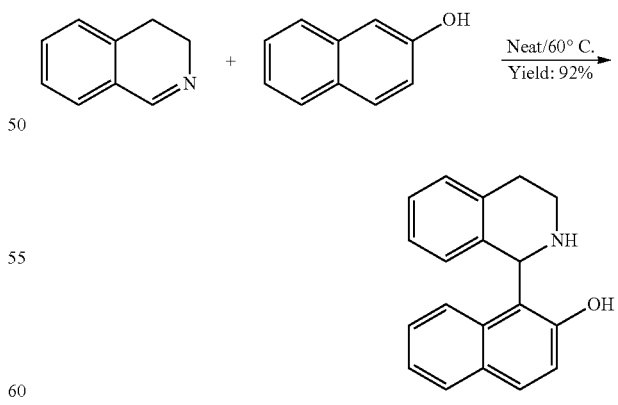

As illustrated hereinbelow in Table 1, the nature of the substituent on the naphthol has an impact on the observed product yield. The presence of electron-donating substituents result in higher product yields (entries 1-4) whereas electron-withdrawing substituents result in lower product yields (entries 6 and 7).

Table 1: Reactions between 3,4-dihydroisoquinoline and naphthols.[a]

TABLE 1

Reactions between 3,4-dihydroisoquinoline and naphthols.[a]

| Entry | Naphthol | Product | Yield (%)[b] |
|---|---|---|---|
| 1 | 7-methoxy-2-naphthol | 1-(7-methoxy-2-hydroxynaphth-1-yl)-1,2,3,4-tetrahydroisoquinoline | 91 |
| 2 | 3-methoxy-2-naphthol | 1-(2-hydroxy-3-methoxynaphth-1-yl)-1,2,3,4-tetrahydroisoquinoline | 81 |
| 3 | 6-methoxy-2-naphthol | 1-(6-methoxy-2-hydroxynaphth-1-yl)-1,2,3,4-tetrahydroisoquinoline | 84[c] |
| 4 | 2,4-dihydroxynaphthalene | 1-(2,4-dihydroxynaphth-1-yl)-1,2,3,4-tetrahydroisoquinoline | 83 |
| 5 | 2,7-dihydroxynaphthalene | 1-(2,7-dihydroxynaphth-1-yl)-1,2,3,4-tetrahydroisoquinoline | 41[e] |
| 6 | 6-benzoyl-2-naphthol | 1-(6-benzoyl-2-hydroxynaphth-1-yl)-1,2,3,4-tetrahydroisoquinoline | 54 |

TABLE 1-continued

Reactions between 3,4-dihydroisoquinoline and naphthols.[a]

| Entry | Naphthol | Product | Yield (%)[b] |
|---|---|---|---|
| 7 | 6-bromo-2-naphthol | 1-(6-bromo-2-hydroxynaphthalen-1-yl)-1,2,3,4-tetrahydroisoquinoline | 45[e] |

[a]Conditions: 3,4-dihydroisoquinoline (1.0 mmol), naphthol (1.0 mmol) at 60° C.; otherwise noted;
[b]Determined by $^1$H NMR spectroscopy using an internal standard;
[c]At 90° C.;
[d]On a 0.2 mmol scale;
[e]Isolated yield following crystallization.

Additional non-limiting examples of chiral ligands as contemplated by the present disclosure are illustrated hereinbelow in Table 2.

TABLE 2

Additional 3,4-dihydroisoquinoline-based ligands.

| Entry | Naphthol | Solvent | T (° C.) | Yield (%)[a] |
|---|---|---|---|---|
| 1 | 2-naphthol | Neat | 60 | 92 (87)[b] |
| 2 | 2-naphthol | Neat | 90 | 83 |
| 3 | 2-naphthol | Toluene | 60 | 41 |
| 4 | 2-naphthol | THF | 60 | 6 |
| 5 | 2-naphthol | DCE | 60 | 20 |
| 6 | 2-naphthol | Neat | 90 (Microwave) | 66 |
| 7 | 1-naphthol | Neat | 60 | 73 |

TABLE 2-continued
Additional 3,4-dihydroisoquinoline-based ligands.
| Entry | Naphthol | Solvent | T (° C.) | Yield (%)[a] |
|---|---|---|---|---|
| 8 | 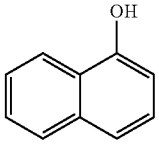 | Neat | 90 | 92 |
| 9 | 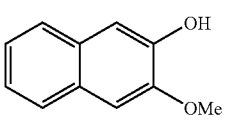 | Neat | 60 | 81 |
| 10 | 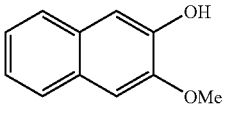 | Neat | 90 | 60[b] |
| 11 | 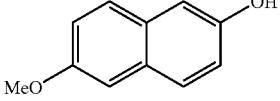 | Neat | 60 | 62 |
| 12 | 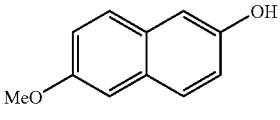 | Neat | 90 | 84 |
| 13 | 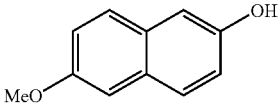 | Neat | 25 | NR |
| 14 | 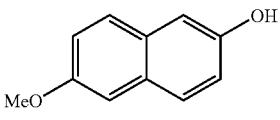 | Neat | 120 | Decomp. |
| 15 | 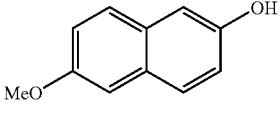 | MeOH | 60 | 12 |
| 16 | 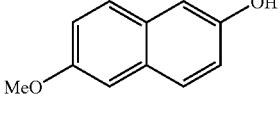 | $CH_3CN$ | 60 | 6 |
| 17 | 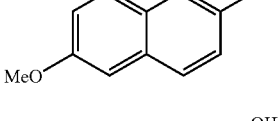 | Ether | Reflux | NR |
| 18 | 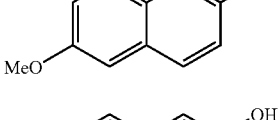 | $CH_3NO_2$ | 60 | 9 |
| 19 | 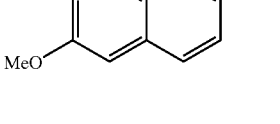 | $H_2O$ | 60 | 66 |

TABLE 2-continued

Additional 3,4-dihydroisoquinoline-based ligands.

| Entry | Naphthol | Solvent | T (° C.) | Yield (%)[a] |
|---|---|---|---|---|
| 20 | 6-MeO-2-naphthol (2,6-isomer with MeO) | CH$_2$Cl$_2$ | Reflux | NR |
| 21 | 7-MeO-2-naphthol | Neat | 60 | 91 |
| 22 | 7-MeO-2-naphthol | Neat | 90 | 97 |
| 23 | 6-Br-2-naphthol | Neat | 60 | 32 |
| 24 | 6-Br-2-naphthol | Neat | 90 | 45[b] |
| 25 | 6-benzoyl-2-naphthol | Neat | 60 | 54 |
| 26 | 6-benzoyl-2-naphthol | Neat | 90 | 12 |
| 27 | naphthalene-1,7-diol | Neat | 60 | 52 (Mixture) |
| 28 | naphthalene-1,7-diol | Neat | 90 | 62 (Mixture) |
| 29 | naphthalene-2,7-diol | Neat | 60 | 41[b] (Impure or Mixture) |
| 30 | naphthalene-2,7-diol | Neat | 90 | 37 |

TABLE 2-continued

Additional 3,4-dihydroisoquinoline-based ligands.

| Entry | Naphthol | Solvent | T (° C.) | Yield (%)[a] |
|---|---|---|---|---|
| 31 | 1,3-dihydroxynaphthalene (1-OH, 3-OH) | Neat | 60 | >99 (Decomp.) |
| 32 | 1,3-dihydroxynaphthalene | Neat | 90 | 27 (Decomp.) |
| 33 | 2,3-dihydroxynaphthalene | Neat | 60 | 85[b] (Impure or Mixture) |
| 34 | 3-hydroxy-N-phenyl-2-naphthamide | Neat | 90 | 89[b] (Impure or Mixture) |
| 35 | methyl 3-hydroxy-2-naphthoate | Neat | 60 | 11 |

[a] 1H NMR Yield (unless otherwise indicated);
[b] Isolated Yield.

In an embodiment, the present disclosure relates to the enantioselective preparation of 3,4-dihydroisoquinoline-based ligands. Resolution of (1,2,3,4-tetrahydro-isoquinolin-1-yl)-naphthale-2-ol (THIQNOL®) using L-tartaric acid in $CH_2Cl_2$ provided an enantiomeric excess (ee) of about 30%. Alternatively, (1,2,3,4-tetrahydro-isoquinolin-1-yl)-naphthale-2-ol can be methylated using $CH_3I$ to provide the corresponding methylated product in high yield. The racemic product is conveniently resolved using L-tartaric acid providing the desired product in excess of 99% ee (Scheme 5).

Scheme 5

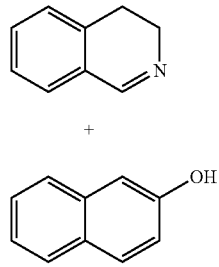

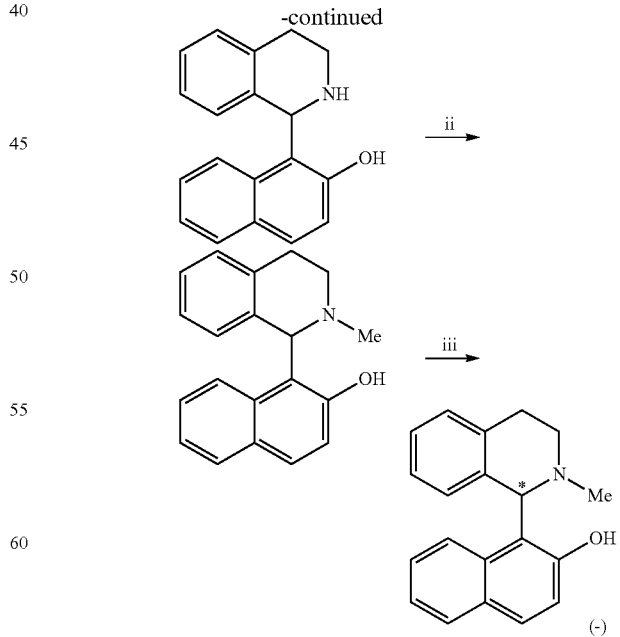

i) Neat, 60° C., 92%; ii) MeI, $KHCO_3$, DMF, RT, 98%; iii) 0.5 equiv. L-tartaric acid, DCM, EtOH, >99% ee.

The reaction of 3,4-dihydroisoquinoline with a chiral acyl chloride, followed by coupling with a naphthol derivative, yielded the corresponding pair of diastereomeric products 4a and 5a as well as 4f and 5f respectively. Subsequent reduction using lithium aluminum hydride yielded the desired chiral products 6 and 7 with high enantiopurity (90-97% ee) (Scheme 6). Other chiral agents suitable for coupling with 3,4-dihyfroisoquinoline are known in the art, and are within the capacity of a skilled technician.

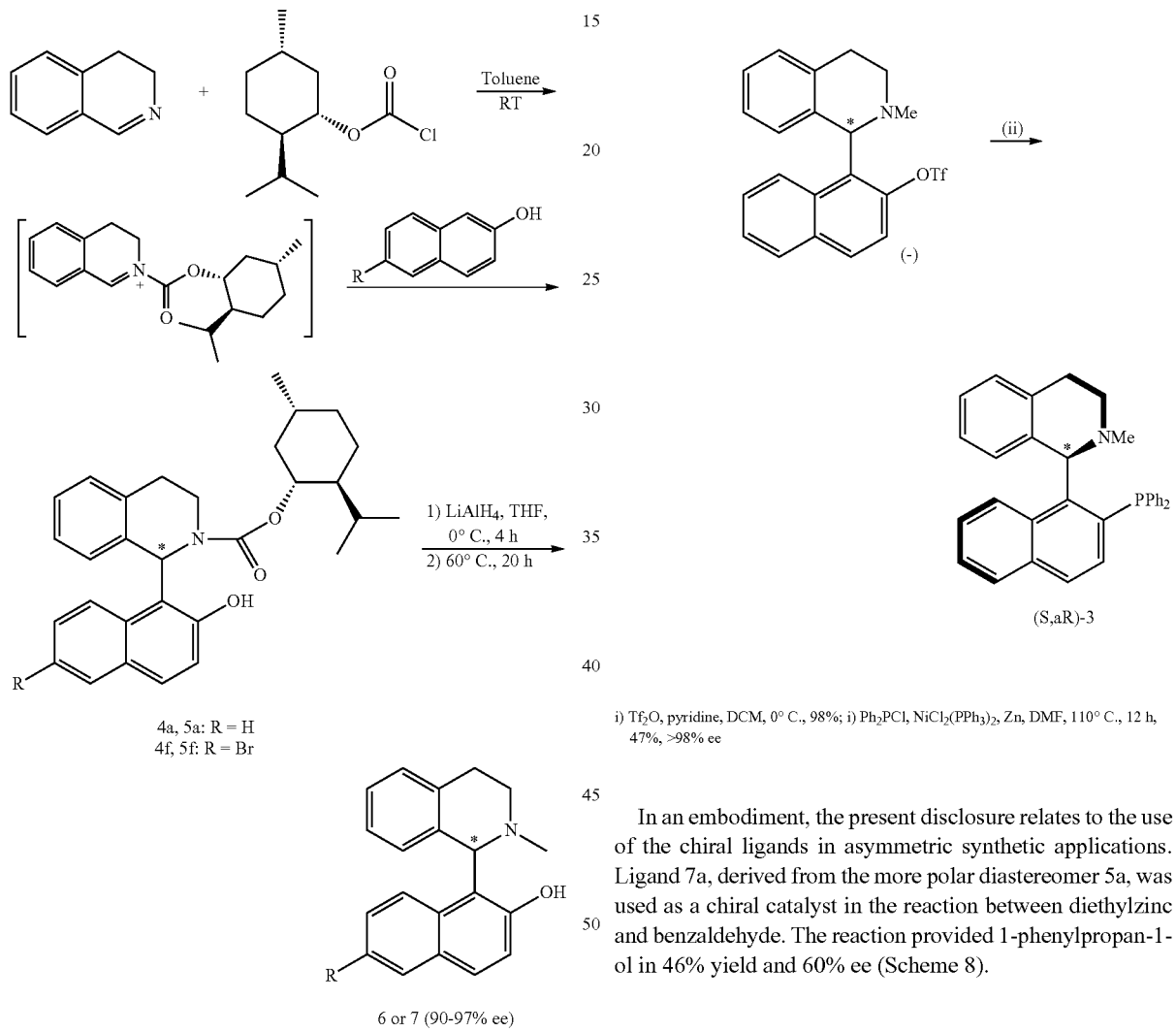

Scheme 6

4a, 5a: R = H
4f, 5f: R = Br 6 or 7 (90-97% ee)

In an embodiment, the present disclosure relates to chiral amino phosphine ligands. Treatment of (−) [1-(2-methyl-1,2,3,4-tetrahydro-isoquinolin-1-yl)-naphthale-2-ol] with trifluoromethanesulfonic anhydride in the presence of pyridine yielded the corresponding triflate derivative in 98% yield. Subsequent phosphination yielded the desired (S, aR)-3 N,P-ligand in 47% yield (Scheme 7). The structure and configuration was confirmed by x-ray single crystal analysis. The ee of the ligand, relative to the chiral alcohol, was retained by more than 98%, as confirmed by chiral HPLC.

Scheme 7

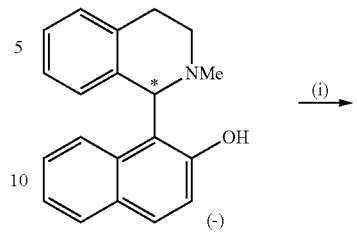

i) Tf₂O, pyridine, DCM, 0° C., 98%; i) Ph₂PCl, NiCl₂(PPh₃)₂, Zn, DMF, 110° C., 12 h, 47%, >98% ee In an embodiment, the present disclosure relates to the use of the chiral ligands in asymmetric synthetic applications. Ligand 7a, derived from the more polar diastereomer 5a, was used as a chiral catalyst in the reaction between diethylzinc and benzaldehyde. The reaction provided 1-phenylpropan-1-ol in 46% yield and 60% ee (Scheme 8).

Scheme 8

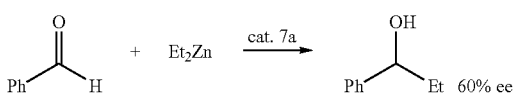

In an embodiment, the present disclosure relates to the use of a chiral N,P-ligand in asymmetric synthetic applications. Ligand (S, aR)-3 was used as a chiral catalyst in the Pd(0)-catalyzed allylic substitution of racemic 1,3-diphenylprop-2-en-1-yl acetate with dimethyl malonate (Table 3).

TABLE 3

Asymmetric Pd(0)-catalyzed allylic substitution of racemic 1,3-diphenylprop-2-en-1-yl acetate with dimethyl malonate.

| Entry | Conditions | Time (h) | Yield (%)[a] | ee (%)[b] |
|---|---|---|---|---|
| 1 | $CH_2Cl_2$, BSA, KOAc, [(allyl)PdCl]$_2$, rt | 48 | 91 | 68 |
| 2 | $CH_2Cl_2$, BSA, KOAc, [(allyl)PdCl]$_2$, −25° C. | 48 | 74 | 78 |
| 3 | $CH_2Cl_2$, BSA, KOAc, Pd$_2$(dba)$_3$ CHCl$_3$, −25° C. | 48 | 82 | 53 |
| 4 | THF, BSA, KOAc, [(allyl)PdCl]$_2$, −25° C. | 48 | 68 | 15 |
| 5 | Toluene, BSA, KOAc, [(allyl)PdCl]$_2$, −25° C. | 48 | trace | nd |
| 6 | $CH_2Cl_2$, BSA, LiOAc, [(allyl)PdCl]$_2$, −25° C. | 48 | 85 | 37 |
| 7 | $CH_2Cl_2$, BSA, CsOAc, [(allyl)PdCl]$_2$, −25° C. | 48 | 79 | 40 |
| 8 | $CH_2Cl_2$, Cs$_2$CO$_3$, [(allyl)PdCl]$_2$, −25° C. | 48 | 95 | −44 |

[a]Isolated yield;
[b]Determined by HPLC on Chiralpak AD column; the absolute configuration of the product was assigned as R (by comparing the retention time with the reported value).

As can be observed from the results in Table 3, decreasing the reaction temperature leads to a significant improvement in the enantioselectivity of the reaction (entry 2 vs 1). The use of Pd$_2$(dba)$_3$ CHCl$_3$ in turn lead to a decrease in the enantioselectivity of the reaction (entries 3 vs 2). Carrying out the reaction in either THF or toluene did neither improve the reaction yield nor the enantioselectivity (entries 4 and 5). Changing the base has substantially no effect on the reaction yield (entries 6 and 7). However, the enantioselectivity decreased significantly.[9] The R configuration was assigned to the allylic substitution product by comparing the retention time of the major enantiomer with literature reports.[10] It should be noted that when Cs$_2$CO$_3$ was used as the base, the absolute configuration of the product changed from R to S (entry 8).

Experimental

General information: $^1$H NMR spectra were recorded on Varian 300 and 400 MHz spectrometers and the chemical shifts were reported in parts per million (δ) relative to internal standard TMS (0 ppm) for CDCl$_3$. The peak patterns are indicated as follows: s, singlet; brs, broad singlet; d, doublet; t, triplet; dt, doublet of triplet; dq, doublet of quartet; dd, doublet of doublet; ddd, doublet of doublet of doublet; dtd, doublet of triplet of doublet; m, multiplet; q, quartet. The coupling constants "J" are reported in Hertz (Hz). $^{13}$C NMR spectra were recorded using 75 and 100 MHz spectrometers and referenced to the internal solvent signals (central peak is 77.00 ppm in CDCl$_3$). HRMS were obtained using a Kratos MS25RFA Mass Spectrometer. IR spectra were recorded using an ABB Bomem MB100 instrument. Melting points were recorded using a Melting Point Apparatus, Gallenkamp. All reagents were weighed and handled in air at room temperature. All regents were purchased from Aldrich except 3,4-dihydroisoquinoline, which was prepared from 1,2,3,4-tetrahhydroisoquinoline according to literature procedures.[11] All reagents were used without further purification.

General procedure for preparing 3,4-dihydroisoquinoline-based ligands: A naphthol derivative (1.0 mmol) was placed in a flask under a nitrogen atmosphere followed by the addition of 3,4-dihydroisoquinoline (1.0 mmol). The resulting mixture was stirred for 16 hours at 60° C., whereupon no liquid remained. The resulting mixture was recrystallized from chloroform and hexane and subsequently collected to yield the desired product ligand.

1-(1,2,3,4-Tetrahydro-isoquinolin-1-yl)-naphthalen-2-ol. Melting Point: 148-150° C.; IR (KBr pellet): $v_{max}$ 3289(m), 3056(w), 3018(w), 2954(w), 2921(w), 2886(w), 2834(w), 1622 (m), 1597 (m), 1462 (m), 1230 (s), 807 (s), 738 (s) cm$^{-1}$; $^1$H NMR (CDCl$_3$, 400 MHz, ppm): δ 8.01 (d, J=8.8 Hz, 1H), 7.79 (d, J=7.6 Hz, 1H), 7.49 (t, J=8.4 Hz, 1H), 7.33 (t, J=7.6 Hz, 1H), 7.08 (m, 3H), 6.87 (m, 1H), 6.61 (d, J=7.6 Hz, 1H), 6.03 (s, 1H), 3.53 (m, 1H), 3.28 (m, 2H), 2.89 (d, J=14 Hz, 1H); $^{13}$C NMR (CDCl$_3$, 75 MHz, ppm): 155.83, 149.66, 136.17, 133.84, 129.64, 128.78, 128.60, 126.89, 126.85, 126.63, 126.16, 122.50, 121.31, 120.15, 55.67, 43.99, 29.39; MS (EI) m/z (%): 275 (M$^+$, 100), 258, 229, 215; HRMS calculated for C$_{19}$H$_{17}$ON, 275.1310; found: 275.1307.

2-(1,2,3,4-Tetrahydro-isoquinolin-1-yl)-naphthalen-1-ol. Melting Point: 117-120° C.; IR (KBr pellet): $v_{max}$ 3305 (m), 3050 (w), 3015 (w), 2950 (w), 2915 (w), 1577 (m), 1491 (m), 1456 (m), 1390 (m), 1121 (m), 1085 (m), 805 (m) cm$^{-1}$; $^1$H NMR (CDCl$_3$, 400 MHz, ppm): δ 8.18 (d, J=8.4 Hz, 1H), 7.75 (d, J=7.6 Hz, 1H), 7.40 (m, 2H), 7.32 (d, J=8.0 Hz, 1H), 7.22 (m, 1H), 7.13 (d, J=4.0 Hz, 2H), 7.00 (m, 1H), 6.88 (d, J=7.6 Hz, 1H), 5.31 (s, 1H), 3.38 (m, 1H), 3.16 (m, 2H), 2.87 (m, 1H); $^{13}$C NMR (CDCl$_3$, MHz, ppm): δ 152.83, 135.96, 133.82, 133.70, 128.76, 127.40, 127.35, 127.07, 126.55, 126.00, 125.75, 125.49, 124.66, 122.14, 119.44, 117.74, 60.80, 42.21, 28.99; MS (EI) m/z (%): 275 (M$^+$, 100), 258, 229, 215, 144, 132; HRMS calculated for C$_{19}$H$_{17}$ON: 275.1310; found: 275.1307.

3-Methoxy-1-(1,2,3,4-tetrahydro-isoquinolin-1-yl)-naphthalen-2-ol. Melting Point: 154-156° C.; IR (KBr pellet): $v_{max}$ 3284 (m), 3060 (w), 2970 (w), 2933 (w), 2833 (w), 1456 (s), 1423 (s), 1322 (m), 1256 (s), 1119 (m), 745 (m) cm$^{-1}$; $^1$H NMR (CDCl$_3$, 400 MHz, ppm): δ 7.95 (d, J=8.4 Hz), 7.72 (d, J=8.4 Hz), 7.36 (m, 2H), 7.10 (m, 3H), 6.86 (m, 1H) 6.63 (d, J=7.6 Hz, 1H), 6.05 (s, 1H), 3.94 (s, 3H), 3.55 (m, 1H), 3.29

(m, 2H), 2.90 (d, J=14.0 Hz, 1H); MS (EI) m/z (%): 305 (M+), 288, 174, 159, 131 (100); HRMS calculated for $C_{20}H_{19}O_2N$, 305.1416; found: 305.1412.

6-Methoxy-1-(1,2,3,4-tetrahydro-isoquinolin-1-yl)-naphthalen-2-ol. Melting Point: 148-151° C.; IR (KBr pellet): $v_{max}$ 3315 (m), 2963 (w), 2932 (w), 2835 (w), 1601 (s), 1517 (m), 1384 (m), 1366 (m), 1246 (s), 1160 (m), 1034 (m), 866 (m) cm$^{-1}$; $^1$H NMR (CDCl$_3$, 400 MHz, ppm): δ 7.92 (d, J=9.6 Hz, 1H), 7.61 (d, J=9.2 Hz, 1H), 7.16 (m, 5H), 6.87 (m, 1H), 6.59 (d, J=8.0 Hz, 1H), 5.97 (s, 1H), 3.92 (s, 3H), 3.52 (m, 1H), 3.27 (m, 2H), 2.89 (d, J=14.4 Hz, 1H); $^{13}$C NMR (CDCl$_3$, 100 MHz, ppm): δ 154.97, 153.91, 136.12, 133.77, 129.00, 128.54, 128.20, 126.77, 126.54, 126.07, 122.90, 120.49, 119.16, 118.45, 107.01, 55.83, 55.33, 43.93, 29.37; MS (EI) m/z (%): 305 (M+, 100), 288, 261, 125, 174, 151, 131; HRMS calculated for $C_{20}H_{19}O_2N$, 305.1416; found: 305.1418.

7-Methoxy-1-(1,2,3,4-tetrahydro-isoquinolin-1-yl)-naphthalen-2-ol. Melting Point: 126-130° C.; IR (KBr pellet): $v_{max}$ 3527 (w), 3286 (m), 2990.0 (w), 2961 (w), 2889 (w), 2837 (w), 1622 (s), 1517 (m), 1482, (m), 1387 (m), 1221 (s), 1135 (m), 1032 (m) 829 (s) cm$^{-1}$; $^1$H NMR (CDCl$_3$, 400 MHz, ppm): δ 7.68 (d, J=8.4 Hz, 1H), 7.62 (d, J=8.4 Hz, 1H), 7.27 (d, J=2 Hz, 1H), 7.10 (m, 4H), 6.93 (m, 4H), 6.67 (d, J=8.0 Hz, 1H), 5.91 (s, 1H), 3.86 (s, 3H), 3.49 (m, 1H), 3.25 (m, 2H), 2.87 (d, J=14.8 Hz, 1H); $^{13}$C NMR (CDCl$_3$, 100 MHz, ppm): δ 158.64, 156.42, 136.15, 134.54, 133.81, 130.28, 129.40, 128.62, 126.81, 126.63, 126.23, 123.62, 117.54, 114.51, 100.67, 55.93, 44.02, 29.38; MS (EI) m/z (%): 305 (M+), 288, 174, 131 (100); HRMS calculated for $C_{20}H_{19}O_2N$: 305.1416; found: 305.1413.

6-Bromo-1-(1,2,3,4-tetrahydro-isoquinolin-1-yl)-naphthalen-2-ol. Compound washed with CHCl$_3$ for purification. Melting point: 168-170° C.; $^1$H NMR (CDCl$_3$, 400 MHz, ppm): δ 7.94 (d, J=2.0 Hz, 1H), 7.88 (d, J=8.8 Hz, 1H), 7.61 (d, J=8.4 Hz, 1H), 7.55 (dd, 1H, J=2.0, 9.0 Hz), 7.10 (m, 3H), 6.89 (m, 1H), 6.54 (d, J=7.6 Hz, 1H), 5.98 (s, 1H), 3.55 (m, 1H), 3.28 (m, 2H), 2.90 (d, J=14.4 Hz, 1H); $^{13}$C NMR (CDCl$_3$, 75 MHz, ppm) δ 156.24, 135.77, 133.86, 131.92, 130.64, 129.97, 129.41, 128.78, 128.72, 126.81, 126.73, 126.25, 123.21, 121.35, 118.30, 115.97, 55.75, 43.96, 29.34; MS (EI) m/z (%): 353 (M+, 100) 324, 309, 257, 228, 132; HRMS calculated for $C_{19}H_{16}ON^{79}Br$: 353.0415; found: 353.0407; HRMS calculated for $C_{19}H_{16}ON^{81}Br$: 355.0395; found: 355.0403.

[6-Hydroxy-5-(1,2,3,4-tetrahydro-isoquinolin-1-yl)-naphthalen-2-yl]-phenyl-methanone. Addition of 6-benzoyl-2-naphthol (50 mg, 0.2 mmol) to 3,4-dihydroisoquinoline (22 μL, 0.2 mmol). Melting point: 138-142° C.; $^1$H NMR (CDCl$_3$, 400 MHz, ppm): δ 8.23 (m, 1H) 8.11 (d, J=8.8 Hz, 1H), 8.02 (d, J=10.8 Hz, 1H), 7.85 (m, 5H), 7.60 (m, 2H), 7.50 (m, 3H), 7.16 (m, 4H), 6.91 (m, 1H), 6.61 (d, J=7.6 Hz, 1H), 6.08 (s, 1H), 3.55 (m, 1H), 3.32 (m, 2H), 2.93 (m, J=12.4 Hz, 1H); MS (EI) m/z (%): 379 (M+), 248, 171 (100), 131; HRMS calculated for $C_{26}H_{21}O_2N$: 379.1572; found: 379.1563.

General procedure for preparing diastereomeric products 4 and 5: A Schlenk under a nitrogen atmosphere was charged with 3,4-dihydroisoquinoline (1.0 mmol). (−)-Menthyl chloroformate (1.0 mmol) and toluene (2 mL) were subsequently added. The reaction mixture was stirred at room temperature over a period of 24 hours. Naphthol or a naphthol derivative (1.0 mmol) was then added and the resulting mixture was stirred for another 24 hours. After being transferred to a round bottom flask comprising chloroform, the solvent was removed and the resulting diastereomers were separated by flash column chromatography on silica gel (hexane/dichloromethane=2:1, 1:1).

(2S,5R)-1-(2-hydroxynaphthalen-1-yl)-3,4-dihydroisoquinolin-2(1H)-yl 2-isopropyl-5-methylcyclohexanecarboxylate (4a) (less polar diastereoisomer). $^1$H NMR (CDCl$_3$, 500 MHz, ppm): δ 7.72-7.68 (m, 2H), 7.45 (brs, 1H), 7.28-7.23 (m, 2H), 7.16-7.13 (m, 2H), 7.08-7.07 (m, 1H), 6.97 (t, J=7.0 Hz, 1H), 6.90 (s, 1H), 6.78 (d, J=8.0 Hz, 1H), 4.68 (td, J=11.0, 4.0, 1H), 4.43 (dd, J=14.5, 5.0 Hz, 1H), 3.68 (td, J=13.5, 3.0 Hz, 1H), 3.09 (td, J=16.5, 5.5 Hz, 1H), 2.99 (d, J=15.5 Hz, 1H), 1.98 (d, J=12.5 Hz, 1H), 1.86-1.69 (m, 1H), 1.63 (d, J=11.5 Hz, 2H), 1.50-1.41 (m, 1H), 1.33-1.26 (m, 2H), 1.06-0.99 (m, 1H), 0.96-0.77 (m, 10H).

(2S,5R)-1-(6-bromo-2-hydroxynaphthalen-1-yl)-3,4-dihydroisoquinolin-2(1H)-yl 2-isopropyl-5-methylcyclohexanecarboxylate (4f) (less polar diastereomer). $^1$H NMR (CDCl$_3$, 400 MHz, ppm): δ 7.80 (d, J=2.0 Hz, 1H), 7.59 (d, J=8.8 Hz, 1H). 7.26 (d, J=9.2 Hz, 1H), 7.22 (d, J=7.2 Hz, 1H), 7.16 (s, 2H), 7.15-7.08 (m, 2H), 6.95 (t, J=7.6 Hz, 1H), 6.84 (s, 1H), 6.72 (d, J=8.0 Hz, 1H), 4.67 (td, J=10.8, 4.4 Hz, 1H), 4.42 (dd, J=14.0, 4.8 Hz, 1H), 3.59 (td, J=13.6, 3.6 Hz, 1H), 3.13-3.05 (m, 1H), 2.98 (d, J=14.8 Hz, 1H), 1.80 (brs, 1H), 1.63 (d, J=10.8 Hz, 2H), 1.42-1.33 (m, 2H), 1.04-1.00 (m, 1H), 0.93-0.77 (m, 11H); $^{13}$C NMR (CDCl$_3$, 100 MHz, ppm): δ 157.28, 155.76, 135.83, 132.87, 131.20, 131.05, 130.46, 129.58, 128.94, 128.61, 127.32, 126.84, 126.58, 126.10, 121.74, 120.34, 115.91, 77.20, 76.86, 52.30, 47.21, 41.22, 39.42, 34.17, 31.35, 29.66, 26.55, 23.57, 21.97, 20.85, 16.63.

(2S,5R)-1-(6-bromo-2-hydroxynaphthalen-1-yl)-3,4-dihydroisoquinolin-2(1H)-yl 2-isopropyl-5-methylcyclohexanecarboxylate (5f) (more polar diastereomer). $^1$H NMR (CDCl$_3$, 400 MHz, ppm): δ 7.81 (d, J=2.0 Hz, 1 H), 7.58 (d, J=8.8 Hz, 1H), 7.25-7.22 (m, 2H), 7.18 (s, 2H), 7.16-7.12 (m, 2H), 6.97 (t, J=8.0 Hz, 1H), 6.82 (s, 1H), 6.75 (d, J=7.6 Hz, 1H), 4.61 (td, J=10.8, 4.4 Hz, 1H), 4.39 (dd, J=13.6, 4.4 Hz, 1H), 3.61 (td, J=13.6, 3.6 Hz, 1H), 3.17-3.08 (m, 1H), 2.96 (d, J=15.2 Hz, 1H), 1.99-1.96 (m, 1H), 1.81-1.76 (m, 1H), 1.64-1.60 (m, 1H), 1.44-1.43 (m, 1H), 1.31-1.28 (m, 1H), 1.03-0.96 (m, 1H), 0.87-0.74 (m, 8H), 0.67 (d, J=7.2 Hz, 3H); $^{13}$C NMR (CDCl$_3$, 75 MHz, ppm): δ 159.42, 155.58, 135.80, 133.10, 131.30, 131.03, 130.44, 129.45, 128.96, 128.72, 127.28, 126.84, 126.64, 125.91, 121.61, 120.23, 115.90, 77.21, 76.84, 52.44, 47.14, 41.12, 39.46, 34.17, 31.31, 29.44, 26.20, 23.41, 22.04, 20.79, 16.38.

Procedure for the preparation of 1-(2-methyl-1,2,3,4-tetrahydroisoquinolin-1-yl)naphthalen-2-ol: Powdered KHCO$_3$ (690 mg, 6.9 mmol) was added to a solution of 1-(1,2,3,4-tetrahydro-isoquinolin-1-yl)-naphthalen-2-ol (1.85 g, 6.73 mmol) in DMF (60 mL). Following 10 minutes of stirring, CH$_3$I (1.05 g, 7.40 mmol) in DMF (20 mL) was added into the slurry. Upon completion of the reaction (8 h), the mixture was filtered and the solid washed with water and acetone to yield the product as a white powder (1.7 g, 5.9 mmol, 87%). Melting point: 210-212° C.; IR (KBr pellet): $v_{max}$ 2956, 1622, 1516, 821 cm$^{-1}$; $^1$H NMR (CDCl$_3$, 400 MHz, ppm): δ 8.06 (d, J=8.0 Hz, 1H), 7.85-7.71 (m, 2H), 7.52-7.48 (m, 1H), 7.33 (t, J=7.2 Hz, 1H), 7.10-7.03 (m, 3H), 6.84 (t, J=8.0 Hz, 1H), 6.61 (d, J=7.6 Hz, 1H), 5.37 (s, 1H), 3.43-3.38 (m, 1H), 3.34-3.30 (m, 1H), 2.91-2.77 (m, 2H), 2.40 (s, 3H); $^{13}$C NMR (CDCl$_3$, 100 MHz, ppm): δ 155.26, 135.84, 134.04, 133.20, 129.45, 128.90, 128.41, 128.12, 127.32, 126.87, 126.52, 126.23, 122.45, 121.42, 119.72, 117.67, 64.07, 52.87, 43.78, 29.28; HRMS calcd for $C_{20}H_{20}NO$: 290.1539; found: 290.1541.

Procedure for resolution of 1-(2-methyl-1,2,3,4-tetrahydroisoquinolin-1-yl)naphthalen-2-ol: (2R,3R)-Tartaric acid (114 mg, 0.76 mmol) in EtOH (15 mL) was added to racemic 1-(2-methyl-1,2,3,4-tetrahydroisoquinolin-1-yl)naphthalen-2-ol (440 mg, 1.52 mmol), in CH$_2$Cl$_2$ (50 ml). The reaction mixture was stirred overnight at room temperature to afford a white solid. The reaction mixture was subsequently stirred for an additional period of 24 h followed by filtration (300 mg, 0.68 mmol, 45%). The solid was treated with an aqueous NaHCO$_3$ solution, extracted with CH$_2$Cl$_2$ and dried using Na$_2$SO$_4$. The solvent was removed under reduced pressure to afford a white powder 182 mg (0.63 mmol, 41%). The enantiomeric purity, as determined by means of chiral HPLC (Daicel Chiralcel OD-H, hexane/isopropanol=97.5:2.5, flow rate 1.0 mL/min), was in excess of 99% ee. The optical rotation $[\alpha]_D^{20}$ was observed to be −304.67 (c 0.4; CH$_2$Cl$_2$). The mother solution was evaporated to dryness under reduced pressure, yielding a residue which was crystallized from hexane/ethyl acetate to afford a white powder 172 mg (0.60 mmol, 39% yield). The enantiomeric purity (ee), as determined by means of chiral HPLC (Daicel Chiralcel OD-H, hexane/isopropanol=97.5:2.5, flow rate 1.0 mL/min), was 92%.

Procedure for the preparation of (−)-1-(1,2,3,4-tetrahydro-2-methylisoquinolin-1-yl)naphthalen-2-yl trifluoromethanesulfonate: Trifluoromethanesulfonic anhydride (0.7 mL, 4.15 mmol) was slowly added to a solution of (−)-1-(2-methyl-1,2,3,4-tetrahydroisoquinolin-1-yl)naphthalen-2-ol (1.0 g, 3.46 mmol) and pyridine (0.5 mL, 5.12 mmol) in dry CH$_2$Cl$_2$ (20.0 mL) at 0° C. The reaction mixture was stirred over a period of 1 hour and subsequently warmed to room temperature. Following the removal of the solvent under reduced pressure, the residue was submitted to chromatographic separation on silica gel using hexane/EtOAc (10:1) as the eluent system. The desired product was obtained as a light yellow oil (1.42 g, 98%). $[\alpha]_D^{20}$=−81.55 (c 1.8, CH$_2$Cl$_2$); $^1$H NMR (300 MHz, CDCl$_3$): δ 8.39 (d, J=8.1 Hz, 1H), 7.93-7.83 (m, 2H), 7.48-7.09 (m, 4H), 6.92 (t, J=7.7 Hz, 1H), 6.59 (s, 1H), 5.27 (s, 1H), 3.55-3.50 (m, 1H), 3.32-3.27 (m, 1H), 2.99-2.75 (m, 2H), 2.22 (s, 3H); $^{13}$C NMR (CDCl$_3$, 100 MHz, ppm): δ 147.05, 137.33, 133.46, 131.64, 130.90, 130.50, 128.50, 128.27, 128.03, 126.60, 126.20, 123.25, 120.07, 118.51, 116.89, 113.71, 63.99, 54.09, 44.29, 29.67; HRMS calcd for C$_{21}$H$_{19}$NO$_3$SF$_3$(M+1): 422.1032; found: 422.1026.

Procedure for the preparation of (S, aR)-1,2,3,4-tetrahydro-2-methyl-1-(2-(diphenylphosphino)naphthalen-1-yl) isoquinoline: To a solution of 1-(1,2,3,4-tetrahydro-2-methylisoquinolin-1-yl)naphthalen-2-yl trifluoromethanesulfonate (920 mg, 2.2 mmol) and bis(triphenylphosphine) nickel(II) chloride (720 mg, 1.1 mmol) in dry DMF (8 mL) under nitrogen in a Schlenk flask, was added chlorodiphenylphosphine (0.4 mL, 2.2 mmol) and Zn (3×100 mg, 4.6 mmol). The color of the solution gradually changed from blue to dark red. The solution was subsequently heated to 110° C. under a nitrogen atmosphere over a period of 12 h. Upon cooling to room temperature, the solvent was removed under reduced pressure. The resulting residue was dissolved in CH$_2$Cl$_2$ and purified by means of short column chromatography on silica gel, using ethyl acetate as the eluent, followed by column chromatography on silica gel using ethyl acetate/hexane. 1:1 as the eluent system. The desired product was obtained as a colorless solid (472 mg, 47% yield). $^1$H NMR (300 MHz, CDCl$_3$): δ 8.44 (d, J=8.1 Hz, 1H), 7.71-6.76 (m, 16H), 6.42 (s, 1H), 3.52 (m, 1H), 3.25 (m, 1H), 2.96-2.80 (m, 2H), 2.05 (s, 3H); $[\alpha]_D^{20}$: −130.52 (c 1.4, CHCl$_3$); $^{31}$P NMR (121.46 MHz, CDCl$_3$): δ −16.0; HRMS calcd for C$_{32}$H$_{29}$NP(M+1): 458.2032; found: 458.2025. The enantiomeric purity (ee), as determined by means of chiral HPLC (Daicel Chiralcel OD-H, hexane/isopropanol=90:10, flow rate 0.5 mL/min), was >98%.

General procedure for preparing products 6 and 7: Dry THF (3 mL) was introduced into a Schienk under a nitrogen atmosphere and cooled to 0° C. Lithium aluminum hydride (0.1 mmol) and compound 4 or 5 were added to the system which was allowed to warm to room temperature over a period of 5 hours. The mixture was then heated at 60° C. for a period of 24 hours. Following completion of the reaction, the mixture was cooled to 0° C. and quenched with water (4 mL). The reaction mixture was subsequently washed with dichloromethane (3×5 mL) followed by washing with a saturated aqueous sodium chloride solution. The organic layer was dried using anhydrous magnesium sulfate and filtered. Upon removal of the solvent, the mixture was separated by thin layer chromatography (hexane/ethyl acetate, 1:1). The fraction having an R$_f$ of 0.8 was collected. The fraction was subsequently extracted with chloroform and washed with hexane to yield the product as white solid.

1-(2-Methyl-1,2,3,4-tetrahydroisoquinolin-1-yl)naphthalen-2-ol (6a) (from less polar diastereoisomer). HPLC (Daicel Chiralcel OD-H, hexane/isopropanol=2:1, flow rate=0.5 mL/min): t$_R$=9.9 min, t$_R$=12.1 min, ee=97%; $^1$H NMR (CDCl$_3$, 400 MHz, ppm): δ 11.89 (brs, 1H), 8.06 (d, J=8.0 Hz, 1H), 7.79 (d, J=8.4 Hz, 1H), 7.52-7.48 (m, 1H), 7.33 (t, J=7.2 Hz, 1H), 7.10-7.03 (m, 3H), 6.84 (t, J=8.0 Hz, 1H), 6.61 (d, J=7.6 Hz, 1H), 3.43-3.38 (m, 1H), 3.34-3.30 (m, 1H), 2.91-2.77 (m, 2H), 2.40 (s, 3H).

1-(2-Methyl-1,2,3,4-tetrahydroisoquinolin-1-yl)naphthalen-2-ol (7a) (from more polar diastereoisomer). HPLC (Daicel Chiralcel OD-H, hexane/isopropanol=2:1, flow rate=0.5 mL/min): t$_R$=9.8 min, t$_R$=11.9 min, ee=94%; $^1$H NMR (CDCl$_3$, 400 MHz, ppm): δ 11.89 (brs, 1H), 8.06 (d, J=8.0 Hz, 1H), 7.79 (d, J=8.4 Hz, 1H), 7.52-7.48 (m, 1H), 7.33 (t, J=7.2 Hz, 1H), 7.10-7.03 (m, 3H), 6.84 (t, J=8.0 Hz, 1H), 6.61 (d, J=7.6 Hz, 1H), 3.43-3.38 (m, 1H), 3.34-3.30 (m, 1H), 2.91-2.77 (m, 2H), 2.40 (s, 3H).

1-Phenylpropan-1-ol. Diethylzinc (1 M in heptane; 1 mL) was introduced into a Schlenk under a nitrogen atmosphere. Toluene (0.5 mL), ligand 7a (0.04 mmol in 0.5 mL toluene) and benzaldehyde (0.5 mmol) were subsequently added. The reaction mixture was stirred at room temperature over a period of 24 hours, cooled to 0° C. and subsequently quenched with an aqueous HCl solution (2M, 5 mL). The reaction mixture was washed with diethyl ether (3×5 mL), followed by washing with a saturated aqueous sodium chloride solution. The organic layer was dried using anhydrous magnesium sulfate and filtered. Upon removal of the solvent, the product was isolated by means of thin layer chromatography (hexane/ethyl acetate, 5:1). The fraction having an R$_f$ of 0.37 was collected. The fraction was subsequently extracted with chloroform to yield the product as a yellow oil. HPLC (Daicel Chiralcel OD-H, hexane/isopropanol=97.5:2.5, flow rate=0.5 mL/min): t$_R$=25.1 min, t$_R$=28.3 min, ee=60%; $^1$H NMR (CDCl$_3$, 300 MHz, ppm): δ 7.34-7.20 (m, 5H), 4.54 (t, J=6.0 Hz, 1H), 2.54 (brs, 1H), 1.86-1.64 (m, 2H), 0.88 (t, J=6.0 Hz, 3H).

General procedure for the asymmetric Pd(0)-catalyzed allylic substitution reaction: To a Schlenk tube comprising (±) 1,3-diphenylprop-2-en-1-yl acetate (252 mg, 1.0 mmol), [Pd (allyl)Cl]$_2$ (3.7 mg, 0.01 mmol, 1 mol %), was added (S, aR)-1,2,3,4-tetrahydro-2-methyl-1-(2-(diphenylphosphino) naphthalen-1-yl)isoquinoline (9.0 mg, 0.02 mmol, 2 mol %) in CH$_2$Cl$_2$ (2 mL). The reaction mixture was stirred at room temperature over a period of 30 minutes. Dimethyl malonate (396 mg, 3.0 mmol), KOAc (2.8 mg, 0.02 mmol) and BSA (613 mg, 3.0 mmol) were subsequently added at −78° C. The reaction mixture was stirred at −25° C. over a period of 48 hours, quenched using a saturated aqueous NH$_4$Cl, solution and extracted with EtOAc (3×5 mL). The organic phase was washed with a saturated aqueous NaHCO$_3$ solution, brine, dried using Na$_2$SO$_4$, and concentrated under reduced pressure. The residue was purified by means of flash chromatography on silica gel using hexane/EtOAc (6:1) as the eluent system to yield the desired product as a colorless oil (78% ee). $^1$H NMR (300 MHz, CDCl$_3$): δ 3.54 (s, 3H), 3.70 (s, 3H), 3.96 (d, J=10.8 Hz, 1H), 4.25 (dd, J=10.8, 8.7 Hz, 1H), 6.33 (dd, J=15.4, 8.6 Hz, 1H), 6.46 (d, J=15.8 Hz, 1H), 7.17-7.24 (m, 10H). The enantiomeric purity (ee), as determined by means of chiral HPLC (Chiralpak AD, hexane/isopropanol=90:10, flow rate 1.0 mL/min); ($t_R$=9.4 min., $t_S$=12.7 min).

Procedure for the preparation of 1-(2-ethyl-1,2,3,4-tetrahydroisoquinolin-1-yl)naphthalen-2-ol: To a solution of 1-(1,2,3,4-tetrahydroisoquinolin-1-yl)-naphthalen-2-ol (0.550 g, 2.0 mmol) in DMF (17 mL), powdered KHCO$_3$ (0.204 g, 2.1 mmol) was added. The resulting slurry was stirred at room temperature for 10 minutes, followed by the dropwise addition of iodoethane (0.9 mL, 5.0 mmol) in DMF (12 mL). After stirring for 22 hours, dichloromethane was added to the reaction mixture and the solution was washed with water to remove the DMF. The organic layer was dried using MgSO$_4$ and the solvent removed under reduced pressure to yield the crude product. Flash chromatography (hexanes/ethyl acetate=10:1, 5:1) yielded a white powder (0.503 g, 1.7 mmol, 83%). $^1$H NMR (CDCl$_3$, 400 MHz, ppm): δ 12.08 (s, 1H), 8.09 (d, J=8.4 Hz, 1H), 7.82 (d, J=8.4 Hz, 1H), 7.71 (d, J=9.2 Hz, 1H), 7.53 (dt, J=8.4, 1.2 Hz, 1H), 7.35 (t, J=7.6 Hz, 1H), 7.13-7.05 (m, 3H), 6.86 (t, J=7.6 Hz, 1H), 6.65 (d, J=8.0 Hz, 1H), 5.57 (s, 1H), 3.0 (ddd, J=11.2, 5.6, 1.6 Hz, 1H), 3.39-3.31 (m, 1H), 2.74-2.84 (m, 2H), 2.71 (dt, J=12.0, 3.6 Hz, 1H), 2.45 (m, 1H), 1.11 (t, J=7.2 Hz, 3H); $^{13}$C NMR (CDCl$_3$, 125 MHz, ppm): δ 155.6, 136.3, 134.1, 133.7, 129.4, 128.9, 128.4, 128.1, 127.5, 126.9, 126.4, 126.2, 122.4, 121.4, 119.9, 118.0, 61.8, 48.6, 48.2, 29.5, 11.4.

Procedure for the resolution of 1-(2-ethyl-1,2,3,4-tetrahydroisoquinolin-1-yl)naphthalen-2-ol: To a solution of 1-(2-ethyl-1,2,3,4-tetrahydroisoquinolin-1-yl)naphthalen-2-ol (1.847 g, 6.1 mmol) in dichloromethane (8 mL), a solution of L-dibenzoyltartaric acid (2.186 g, 6.1 mmol) in 100% ethanol (34 mL) was added dropwise. The resulting mixture was stirred for 22 hours which led to the formation of a colorless salt. The solid was filtered, suspended in water and treated with an aqueous Na$_2$CO$_3$ solution. After extraction with dichloromethane, the organic phase was dried using MgSO$_4$ and the solvent was removed under reduced pressure to yield a light purple powder (0.813 g, 2.7 mmol, 44%). The enantiomeric purity (ee) was determined by chiral HPLC (Daicel Chiralcel OD-H, hexane/isopropanol=97.5/2.5, flow rate 0.5 mL/min) to be 90%. The mother liquor was evaporated under reduced pressure and the residue subjected to the treatment as described hereinabove. A pale orange solid (0.100 g, 3.3 mmol, 54%) was isolated and its enantiomeric purity (ee) was determined to be 89%. After recrystallization from diethyl ether, a white solid (0.138 g, 0.46 mmol, 7%) was collected and the enantiomeric purity (ee) was found to be 98%. A further recrystallization was performed on the remaining solution and a colorless, crystalline material (0.380 g, 1.3 mmol, 21%) was isolated. The enantiomeric purity (ee) was determined to be >99.5%.

Procedure for the preparation of 1-(2-propyl-1,2,3,4-tetrahydroisoquinolin-1-yl)naphthalen-2-ol: To a solution of 1-(1,2,3,4-tetrahydroisoquinolin-1-yl)-naphthalen-2-ol (1.651 g, 6.0 mmol) in DMF (30 mL), powdered KHCO$_3$ (0.661 g, 6.6 mmol) was added. The resulting slurry was stirred at room temperature for 10 minutes, followed by the dropwise addition of 1-iodopropane (2.4 mL, 30 mmol) in DMF (10 mL). After stirring for 24 hours, dichloromethane was added to the reaction mixture and the solution was washed with water to remove the DMF. The organic layer was dried over MgSO$_4$ and the solvent removed under reduced pressure to yield the crude product. Flash chromatography (hexanes/ethyl acetate=10:1, 5:1) yielded a white powder (1.252 g, 4.0 mmol, 66%). $^1$H NMR (CDCl$_3$, 400 MHz, ppm): δ 12.01 (s, 1H), 8.07 (d, J=8.8 Hz, 1H), 7.77 (d, J=8.0 Hz, 1H), 7.67 (d, J=9.2 Hz, 1H), 7.49 (t, J=7.2 Hz, 1H), 7.30 (t, J=8.0 Hz, 1H), 7.08-7.00 (m, 3H), 6.80 (t, J=7.2 Hz, 1H), 6.63 (d, J=8.0 Hz, 1H), 5.50 (s, 1H), 3.44 (dd, J=11.2, 3.6 Hz, 1H), 3.34-3.27 (m, 1H), 2.85 (d, J=16.4 Hz, 1H), 2.73-2.66 (m, 1H), 2.59 (t, J=12.0 Hz, 1H), 2.33-2.26 (m, 1H), 1.55-1.51 (m, 2H), 0.74 (t, J=7.2 Hz, 3H); $^{13}$C NMR (CDCl$_3$, 125 MHz, ppm): δ 155.4, 136.3, 134.1, 133.6, 129.3, 128.9, 128.4, 128.0, 127.4, 126.8, 126.3, 126.1, 122.4, 121.3, 119.8, 118.2, 62.4, 56.6, 48.7, 29.4, 19.5, 11.5.

Procedure for the resolution of 1-(2-propyl-1,2,3,4-tetrahydroisoquinolin-1-yl)naphthalen-2-ol: To a solution of 1-(2-propyl-1,2,3,4-tetrahydroisoquinolin-1-yl)naphthalen-2-ol (0.317 g, 1.0 mmol) in dichloromethane (1.3 mL), a solution of L-dibenzoyltartaric acid (0.358 g, 1.0 mmol) in 100% ethanol (6.0 mL) was added dropwise. The resulting mixture was stirred for 20 hours which led to the formation of a colorless salt. The solid was filtered, suspended in water and treated with an aqueous Na$_2$CO$_3$ solution. After extraction with dichloromethane, the organic phase was dried using MgSO$_4$ and the solvent was removed under reduced pressure to yield a light purple powder (0.117 g, 0.4 mmol, 40%). The enantiomeric purity (ee) was determined by chiral HPLC (Daicel Chiralcel OD-H, hexane/isopropanol=97.5/2.5, flow rate 0.5 mL/min) to be 95%. The mother liquor was evaporated under reduced pressure and the residue subjected to the treatment as described hereinabove. A pale orange solid (0.197 g, 0.6 mmol, 60%) was isolated and its enantiomeric purity (ee) was determined to be 48%.

Procedure for the preparation of 1-(2-benzyl-1,2,3,4-tetrahydroisoquinolin-1-yl)naphthalen-2-ol: To a solution of 1-(1,2,3,4-tetrahydroisoquinolin-1-yl)-naphthalen-2-ol (1.158 g, 4.2 mmol) in CH$_3$CN (40 mL), powdered KHCO$_3$ (0.429 g, 4.3 mmol) was added. The resulting slurry was stirred at room temperature for 10 minutes, followed by the dropwise addition of benzyl bromide (0.55 mL, 4.6 mmol) in CH$_3$CN ((12 mL). After stirring for 3 days, the solvent removed under reduced pressure to yield the crude product. Flash chromatography (hexanes/ethyl acetate=20:1, 10:1) yielded a pale yellow powder (1.313 g, 3.6 mmol, 86%). $^1$H NMR (CDCl$_3$, 400 MHz, ppm): δ 11.86 (s, 1H), 8.10 (d, J=8.4 Hz, 1H), 7.79 (d, J=7.6 Hz, 1H), 7.71 (d, J=9.2 Hz, 1H), 7.52 (t, J=6.8 Hz, 1H), 7.33 (t, J=7.2 Hz, 1H), 7.28-7.21 (m, 5H), 7.14 (d, J=8.8 Hz, 1H), 7.02 (m, 2H), 6.80-6.78 (m, 1H), 6.67 (d, J=8.0 Hz, 1H), 5.57 (s, 1H), 4.07 (d, J=12.8 Hz, 1H), 3.30 (dd, J=10.8, 4.8 Hz, 1H), 3.23-3.11 (m, 2H), 2.74 (d, J=16.8 Hz, 1H), 2.53 (dt, J=11.6, 2.8 Hz, 1H); $^{13}$C NMR (CDCl$_3$, 125 MHz, ppm): δ 155.1, 136.5, 135.9, 133.7, 129.64, 129.60, 129.0, 128.5, 128.4, 128.1, 127.5, 127.4, 127.0, 126.6, 126.2, 122.6, 121.5, 119.9, 118.1, 62.5, 59.5, 48.4, 29.2.

Procedure for the preparation of 1-(2-methoxynaphthalen-1-yl)-2-methyl-1,2,3,4-tetrahydroisoquinoline: Enantiopure 1-(2-methyl-1,2,3,4-tetrahydroisoquinolin-1-yl)naphthalen-2-ol (0.289 g, 1.0 mmol) was dissolved in THF (3.0 mL) followed by the addition of sodium hydroxide (0.044 g, 1.1 mmol). The pink solution was stirred for 10 minutes, during which time it turned orange in color. Iodomethane (68 µL, 1.1 mmol) was subsequently added and the solution stirred for an additional 20 hours. The mixture was quenched with aqueous NH$_4$Cl solution and filtered. After extraction with dichloromethane and removal of the solvent under reduced pressure, ethanol was added to precipitate any remaining starting material. The precipitate was filtered and the filtrate concentrated under reduced pressure to yield an off-white powder (0.012 g, 0.04 mmol, 4%). $^1$H NMR (CDCl$_3$, 500 MHz, ppm): δ 8.16 (d, J=6.5 Hz, 1H), 7.79 (d, J=9.0 Hz, 1H), 7.69 (d, J=6.5 Hz, 1H), 7.31 (d, J=8.5 Hz, 1H), 7.20-7.14 (m, 3H), 7.03 (t, J=7.5 Hz, 1H), 6.83 (t, J=7.5 Hz, 1H), 6.50 (d, J=8.0 Hz, 1H), 5.45 (s, 1H), 3.97 (s, 3H), 3.49 (m, 1H), 3.25 (dd, J=11.0, 5.0 Hz, 1H), 2.90 (d, J=16.0 Hz, 1H), 2.72 (dt, J=12.0, 3.0 Hz, 1H), 2.15 (s, 3H); $^{13}$C NMR (CDCl$_3$, 125 MHz, ppm): δ 162.6, 156.5, 139.3, 134.0, 132.1, 130.1, 129.6, 128.2, 127.9, 126.8, 126.6, 125.8, 125.4, 123.6, 123.3, 113.2, 62.2, 57.0, 54.4, 44.2, 30.0.

Procedure for the preparation of 1-(2-methoxymethoxy) naphthalen-1-yl)-2-methyl-1,2,3,4-tetrahydroisoquinoline: To a Schlenk charged with NaH (0.919 g, 23 mmol) under a nitrogen atmosphere, DMF (23 mL) was added. To this slurry, 1-(2-methyl-1,2,3,4-tetrahydroisoquinolin-1-yl)naphthalen-2-ol (0.2.894 g, 10 mmol) in DMF (23 mL) was added. The mixture was cooled to 0° C. and MOM-Cl (0.76 mL, 10 mmol) was added. The solution turned bright yellow, was allowed to warm to room temperature and stirred for an additional 17 hours. After being quenched with water, a fluffy white powder precipitated which was isolated by vacuum filtration. The powder was dried in vacuo over a period of 8 hours and collected (3.2 g, 9.6 mmol, 96%). $^1$H NMR (CDCl$_3$, 400 MHz, ppm): δ 8.14 (d, J=8.0 Hz, 1H), 7.77 (d, J=9.2 Hz, 1H), 7.69 (d, J=7.2 Hz, 1H), 7.44 (d, J=8.8 Hz, 1H), 7.23-7.14 (m, 3H), 7.03 (t, J=7.6 Hz, 1H), 6.52 (d, J=8.0 Hz, 1H), 5.45 (s, 1H), 5.33 (d, J=3.2 Hz, 2H), 3.53-3.49 (m, 4H), 3.26 (dd, J=11.6, 4.4 Hz, 1H), 2.91 (d, J=16.0 Hz, 1H), 2.71 (dt, J=12.0, 3.6 Hz, 1 H), 2.16 (s, 3H); $^{13}$H NMR (CDCl$_3$, 125 MHz, ppm): δ 154.1, 139.1, 134.0, 132.1, 130.6, 129.6, 128.2, 127.9, 126.9, 126.6, 125.9, 125.5, 124.3, 123.6, 115.3, 95.2, 62.5, 56.2, 54.4, 44.2, 29.9, 29.7.

Procedure for the preparation of 1-(2-(methoxymethoxy) naphthalen-1-yl)-2-methyl-3-(triphenylsilyl)-1,2,3,4-tetrahydroisoquinoline: To a Schlenk under nitrogen, charged with diethyl ether (5 mL) and TMEDA (0.15 mL, 1.0 mmol), was added dropwise n-butyl lithium (1.6 M in hexanes, 1.6 mL, 2.5 mmol). After stirring at room temperature for 40 minutes, 1-(2-methoxymethoxy)naphthalen-1-yl)-2-methyl-1,2,3,4-tetrahydroisoquinoline (0.333 g, 1.0 mmol) in diethyl ether (5 mL) was added resulting in an orange solution. The mixture was stirred at room temperature for a further 3 hours, resulting in the formation of an orange/brown precipitate. After cooling the reaction mixture to 0° C., Ph$_3$SiCl (0.737 g, 2.5 mmol) in diethyl ether (5 mL) was added. Stirring, while allowing the reaction mixture to warm to room temperature, gave way to a bright orange solution comprising an orange suspension. After stirring for an additional 24 hours, the mixture was quenched with an aqueous NH$_4$Cl solution, extracted with dichloromethane, dried using MgSO$_4$ and filtered. The solvent was subsequently removed under reduced pressure. The crude reaction mixture was purified by means of thin layer chromatography (hexanes/ethyl acetate/triethylamine 3:1:0.4) to yield the desired product (R$_f$=0.75).

Procedure for the preparation of 3-iodo-2-naphthol: Water (0.3 mL) and concentrated HCl (2.0 mL) were added to 3-amino-2-naphthol (0.795 g, 5.0 mmol). The reaction mixture was cooled to 0° C. followed by the addition of an aqueous solution of NaNO$_2$ (0.690 g, 10.0 mmol, 1.0 mL) by means of a syringe pump over a period of one hour. Additional water (2.0 mL) was added 30 minutes into the addition of the NaNO$_2$ solution. An aqueous KI solution (1.66 g, 10.0 mmol, 1.5 mL) was added next over a period of 1 hour by means of a syringe pump. The solution was allowed to warm to room temperature and stirred for an additional 21 hours. The resulting red solution comprised a black tar-like precipitate which was isolated by removal of the aqueous layer. Flash chromatography (hexanes/diethyl ether=4:1) yielded a red/orange solid (0.283 g, 1.05 mmol, 21%). $^1$H NMR (CDCl$_3$, 400 MHz, ppm): δ 8.25 (s, 1H), 7.69-7.65 (m, 2H), 7.46-7.42 (m, 1H), 7.35-7.31 (m, 2H).

Procedure for the preparation of 3-iodo-1-(1,2,3,4-tetrahydro-isoquinolin-1-yl)-naphthalen-2-ol: 3-Iodo-2-naphthol (0.283 g, 1.05 mmol) and 3,4-dihydroisoquinoline (0.138 g, 1.05 mmol) were placed in a flask and put under a nitrogen atmosphere. The resulting mixture was stirred over a period of 16 hours at 60° C., whereupon no liquid remained. Acetone was used to wash the pink powder which was isolated by filtration (0.207 g, 0.52 mmol, 49%).

Procedure for the preparation of 3-iodo-1-(2-methyl-1,2,3,4-tetrahydroisoquinolin-1-yl)naphthalen-2-ol: To a solution of 3-iodo-1-(1,2,3,4-tetrahydro-isoquinolin-1-yl)-naphthalen-2-ol (0.207 g, 0.5 mmol) in DMF (5.0 mL), powdered KHCO$_3$ (0.050 g, 0.5 mmol) was added. The resulting slurry was stirred at room temperature over a period of 10 minutes, followed by the dropwise addition of iodomethane (34 μL, 0.55 mmol). After stirring for 24 hours, dichloromethane was added to the reaction mixture and the solution was washed with water to remove the DMF. The organic layer was dried using MgSO$_4$ and the solvent removed under reduced pressure to yield the crude product. Flash chromatography (hexanes/ethyl acetate=10:1, 5:1) yielded an orange powder (0.073 g, 0.17 mmol, 35%). $^1$H NMR (CDCl$_3$, 400 MHz, ppm): δ 8.30 (s, 1H), 8.05 (d, J=8.4 Hz, 1H), 7.71 (d, J=8.4 Hz, 1H), 7.54 (t, J=7.2 Hz, 1H), 7.35 (t, J=7.2 Hz, 1H), 7.10-7.06 (m, 2H), 6.86 (m, 1H), 6.62 (d, J=8.0 Hz, 1H), 5.34 (s, 1H), 3.44-3.30 (m, 2H), 2.90-2.81 (m, 2H), 2.40 (s, 3H); $^{13}$C NMR (CDCl$_3$, 125 MHz, ppm): δ 153.6, 138.7, 135.0, 133.9, 133.2, 129.8, 128.3, 127.9, 127.4, 127.3, 126.7, 126.3, 123.2, 121.5, 117.9, 89.8, 64.1, 52.5, 43.8, 29.2.

Procedure for the resolution of 3-iodo-1-(2-methyl-1,2,3,4-tetrahydroisoquinolin-1-yl)naphthalen-2-ol: To a solution of 3-iodo-1-(2-methyl-1,2,3,4-tetrahydroisoquinolin-1-yl) naphthalen-2-ol (0.073 g, 0.17 mmol) in dichloromethane (2.5 mL), a solution of L-tartaric acid (0.085 g, 0.09 mmol) in 100% ethanol (0.5 mL) was added dropwise. The resulting mixture was stirred overnight, whereupon the solvent had evaporated. Dichloromethane was added to the residue which yielded an insoluble pale pink solid. The solid was filtered, suspended in water and treated with an aqueous Na$_2$CO$_3$ solution. Following extraction with dichloromethane, the organic phase was dried using MgSO$_4$ and the solvent removed under reduced pressure to yield light purple powder (0.019 g, 0.05 mmol, 25%). The enantiomeric purity (ee) was determined by chiral HPLC (Daicel Chiralcel OD-H, hexane/isopropanol=97.5/2.5, flow rate 1.0 mL/min) to be 58%. The mother liquor was evaporated under reduced pressure and the residue subjected to the treatment as described hereinabove. A pale orange solid (0.054 g, 0.13 mmol, 76%) was isolated and its enantiomeric purity (ee) was determined to be 4%.

It is to be understood that the disclosure is not limited in its application to the details of construction and parts as described hereinabove. The disclosure is capable of other embodiments and of being practiced in various ways. It is also understood that the phraseology or terminology used herein is for the purpose of description and not limitation. Hence, although the present disclosure has been described hereinabove by way of illustrative embodiments thereof, it can be modified, without departing from the spirit, scope and nature as defined in the appended claims.

References

1. For an overview, please see: Noyori, R. Adv. Synth. Catal. 2003, 345, 15.
2. (a) Noyori, R. *Asymmetric Catalysis in Organic Synthesis*; Wiley: New York, 1994; (b) Ojima, I., Ed. *Catalytic Asymmetric Synthesis*, 2nd ed.; Wiley-VCH: New York, 2000.
3. For selected reviews, see: (a) Chelucci, G.; Orru, G.; Pinna, G. A. *Tetrahydron*, 2003, 59, 9471; (b) Guiry, P. J.; Saunders, C. P. *Adv. Synth. Catal.* 2004, 346, 497.
4. For recent reviews, see: (a) Helmchen, G. *J. Organomet. Chem.* 1999, 576, 203; (b) Trost, B. M.; Van Vranken, D. L. *Chem. Rev.* 1996, 96, 395; (c) Johannsen, M.; Jorgensen, K. A. *Chem. Rev.* 1998, 98, 1689; (d) Pfaltz, A.; Lautens, M. *Comprehensive Asymmetric Catalysis*; Jacobsen, E. N., Pfaltz, A., Yamamoto, H., Eds.; Springer: Berlin, 1999; Vol. 2, Chapter 24; (e) Trost, B. M.; Crawley, M. L. *Chem. Rev.* 2003, 103, 2921.
5. For some recent examples of asymmetric allylic substitution of 1,3-disubstituted allyl substrates using P,N-chelating ligands, see: (a) von Matt, P.; Pfaltz, A. Angew. *Chem. Int. Ed. Engl.* 1993, 32, 566; (b) Sprinz, J.; Helmchen, G. *Tetrahedron Lett.* 1993, 34, 1769; (c) Dawson, G. J.; Frost, C. G.; Williams, J. M. J.; Coote, S. J. *Tetrahedron Lett.* 1993, 34, 3149; (d) Brown, J. M.; Hulmes, D. I.; Guiry, P. J. *Tetrahedron* 1994, 50, 4493; (e) Kubota, H.; Koga, K. *Tetrahedron Lett.* 1994, 36, 6689; (f) Wimmer, P.; Widhalm, M. *Tetrahedron: Asymmetry* 1995, 6, 657; (g) Togni, A.; Burckhardt, U.; Gramlich, V.; Pregosin, P. S.; Salzmann, R.; *J. Am. Chem. Soc.* 1996, 118, 1031; (h) Evans, P. A.; Brandt, T. A. *Tetrahedron Lett.* 1996, 37, 9143; (i) Saitoh, A.; Morimoto, T.; Achiwa, K. *Tetrahedron. Asymmetry* 1997, 8, 3567; (j) Brunel, J.-M.; Constantieux, T.; Labande, A.; Lubatti, F.; Buono, G. *Tetrahedron Lett.* 1997, 38, 5971; (k) Bourghida, M.; Widhalm, M. *Tetrahedron: Asymmetry* 1998, 9, 1073; (l) Ogasawara, M.; Yoshida, K.; Kamei, H.; Kato, K.; Uozumi, Y.; Hayashi, T. *Tetrahedron: Asymmetry* 1998, 9, 1779; (m) Zhang, W.; Yoneda, Y.; Kida, T.; Nakatsuji, Y.; Ikeda, 5. Tetrahedron: Asymmetry 1998, 9, 3371; (n) Cahill, J. P.; Guiry, P. J. Tetrahedron: Asymmetry 1998, 9, 4301; (O) Imai, Y.; Zhang, W.; Kida, T.; Nakatsuji, Y.; Ikeda, I. *Tetrahedron Lett.* 1998, 39, 4343; (p) Wiese, B.; Helmchen, G. *Tetrahedron Lett.* 1998, 39, 5727; (q) Yonehara, K.; Hashizume, T.; Mori, K.; Ohe, K.; Uemura, S. Chem. Commun. 1999, 415; (r) Saitoh, A.; Misawa, M.; Morimoto, T. *Synlett,* 1999, 483; (s) Hiroi, K.; Suzuki, Y.; Abe, I. *Tetrahedron: Asymmetry* 1999, 10, 1173; (t) Suzuki, Y.; Ogata, Y.; Hiroi, K. *Tetrahedron: Asymmetry* 1999, 10, 1219; (u) Ito, K.; Kashiwagi, R.; Iwasaki, K.; Katsuki, T. *Synlett,* 1999, 1563.
6. (a) Bentley, K. W. Nat. Prod. Rep. 2004, 21, 395. (b) Bentley, K. W. *Nat. Prod. Rep.* 2005, 22, 249.
7. (a) Chrzanowska, M.; Rozwadowska, M. D. *Chem. Rev.* 2004, 104, 3341. (b) Baran, P. S.; Richter, J. M.; Lin, D. W. *Angew. Chem. Int. Ed.* 2005, 44, 609 and references cited therein.
8. Venkov, A. P.; Statkove, S. M.; Ivanov, I. I. *Synth. Commun.* 1992, 22, 125.
9. For selected examples of counterion effect, see: (a) Trost, B. M.; Bunt, R. C. *J. Am. Chem. Soc.* 1998, 120, 70; (b) Raghunath, M.; Gao, W.; Zhang, X. *Tetrahedron Asymmetry* 2005, 16, 3676.
10. Wang, Y.; Li, X.; Ding, K. *Tetrahedron Asymmetry* 2002, 13, 1291.
11. Pelletier, J. C.; Cava, M. P. *J. Org. Chem.* 1987, 52, 616.

What is claimed is:

1. A chiral ligand of Formula I:

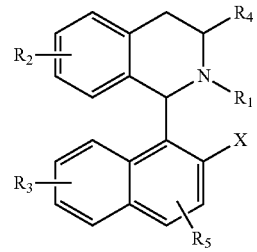

wherein:

$R_1$, $R_2$, $R_3$, $R_4$ and $R_5$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl;

X is selected from the group consisting of OH, $OR_7$, O-Prot and $P(R_7)_2$ where Prot represents a hydroxy protecting group; and $R_6$ and $R_7$ are selected from the group consisting of hydrogen, $C_{1-10}$ alkyl, $C_{2-10}$ alkenyl, $C_{2-10}$ alkynyl, $C_{1-10}$ alkoxy, phenyl, and aryl.

2. The chiral ligand of claim 1, wherein said ligand is selected from the group consisting of:

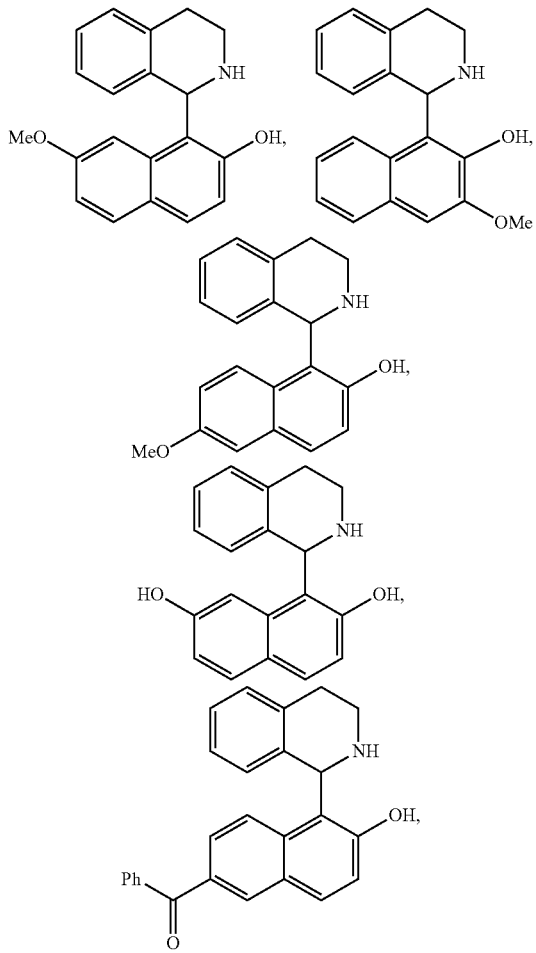

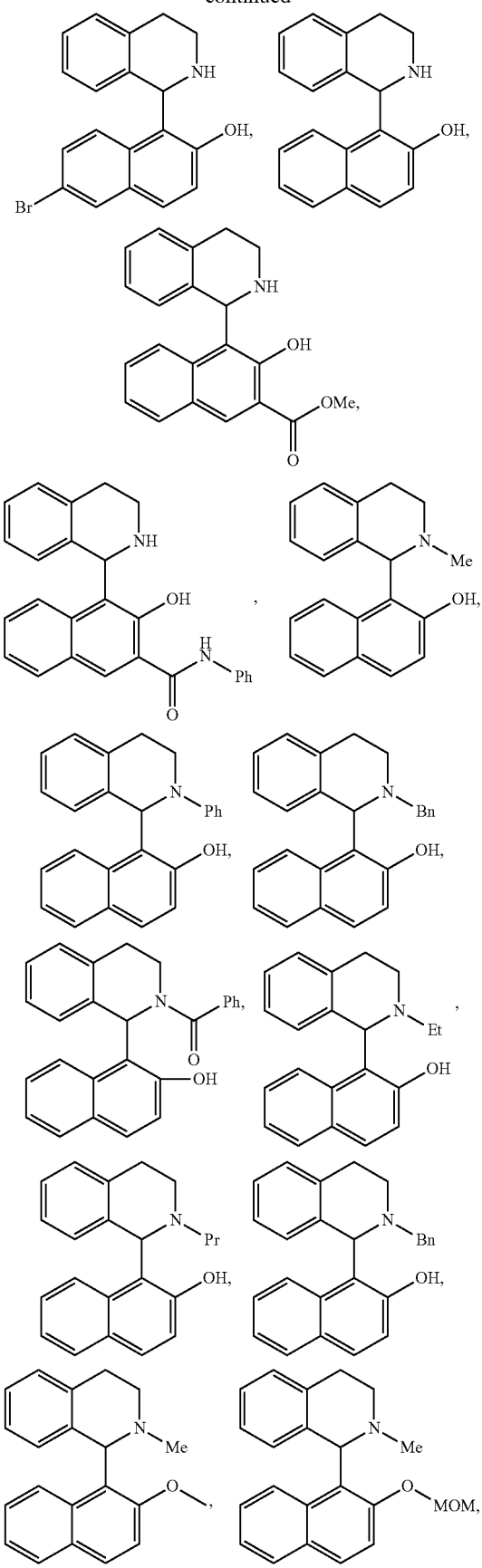

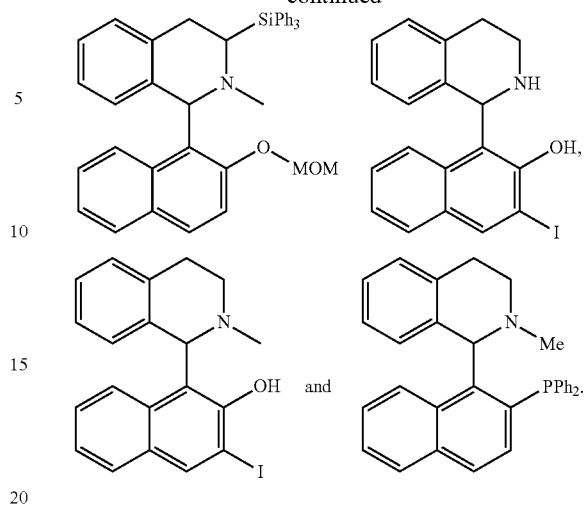

3. The chiral ligand of claim 1, wherein said ligand is a racemic mixture of enantiomers.

4. The chiral ligand of claim 1, wherein said ligand is a non-racemic mixture of enantiomers.

5. The chiral ligand of claim 1, selected from the group consisting of L and R enantiomers.

6. The chiral ligand of claim 5, wherein said ligand comprises the L-enantiomer.

7. The chiral ligand of claim 5, wherein said ligand comprises the R-enantiomer.

8. The chiral ligand of claim 1, wherein said ligand comprises an optical purity of at least 50% ee.

9. The chiral ligand of claim 8, wherein said ligand comprises an optical purity of at least 60% ee.

10. The chiral ligand of claim 8, wherein said ligand comprises an optical purity of at least 70% ee.

11. The chiral ligand of claim 8, wherein said ligand comprises an optical purity of at least 80% ee.

12. The chiral ligand of claim 8, wherein said ligand comprises an optical purity of at least 90% ee.

13. The chiral ligand of claim 8, wherein said ligand comprises an optical purity of at least 95% ee.

14. A process for the preparation of a chiral ligand of Formula I as defined in claim 1, the process comprising:

a) reacting a compound of Formula Ia:

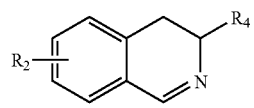

wherein:

$R_2$ and $R_4$ are independently selected from the group consisting of hydrogen, halogen, $C_{1-10}$ alkyl, $C_{2-10}$ alkenyl, $C_{2-10}$ alkynyl, $C_{1-10}$ alkoxy, $C(O)R_6$, $C(O)NHR_6$, $Si(R_6)_3$, benzyl and aryl; and $R_6$ is selected from the group consisting of hydrogen, $C_{1-10}$ alkyl, $C_{2-10}$ alkenyl, $C_{2-10}$ alkynyl, $C_{1-10}$ alkoxy, phenyl, and aryl;

b) with a compound of Formula Ib:

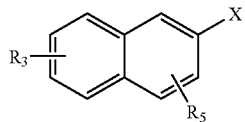

wherein

R$_3$ and R$_5$ are independently selected from the group consisting of hydrogen, halogen, C$_{1-10}$ alkyl, C$_{2-10}$ alkenyl, C$_{2-10}$ alkynyl, Cl-TO alkoxy, C(O)R$_6$, C(O)NHR$_6$, Si(R$_6$)$_3$, benzyl and aryl;

X is selected from the group consisting of OH, OR$_7$, O-Prot and P(R$_7$)$_2$ where Prot represents a hydroxy protecting group; and R$_6$ and R$_7$ are selected from the group consisting of hydrogen, C$_{1-10}$ alkyl, C$_{2-10}$ alkenyl, C$_{2-10}$ alkynyl, C$_{1-10}$ alkoxy, phenyl, and aryl.

* * * * *

UNITED STATES PATENT AND TRADEMARK OFFICE
CERTIFICATE OF CORRECTION

PATENT NO. : 8,232,399 B2
APPLICATION NO. : 12/281267
DATED : July 31, 2012
INVENTOR(S) : Chao-Jun Li et al.

Page 1 of 1

It is certified that error appears in the above-identified patent and that said Letters Patent is hereby corrected as shown below:

On the Title page, item (57) Abstract, line 2, delete

"Formula 1: 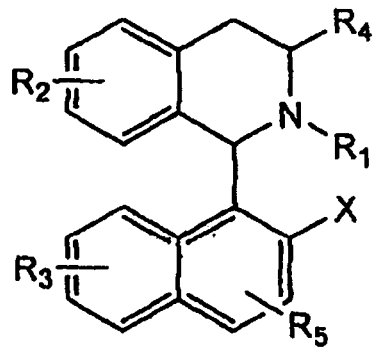 " and insert

--Formula 1: 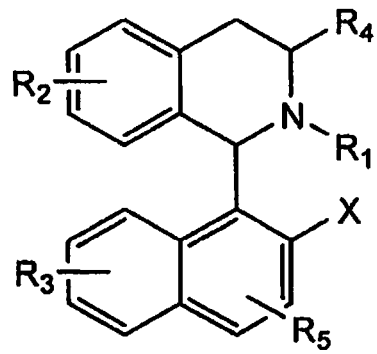 -- therefor.

In claim 14, column 40, line 1, delete "Cl-TO" and insert --$C_{1-10}$-- therefor.

Signed and Sealed this
Twenty-third Day of October, 2012

David J. Kappos
*Director of the United States Patent and Trademark Office*